US007355143B1

(12) United States Patent
Nakano et al.

(10) Patent No.: US 7,355,143 B1
(45) Date of Patent: *Apr. 8, 2008

(54) CIRCUIT BOARD PRODUCTION METHOD AND ITS APPARATUS

(75) Inventors: Hiroyuki Nakano, Yokohama (JP);
 Toshihiko Nakata, Yokohama (JP);
 Masayoshi Serizawa, Yokohama (JP);
 Hideaki Sasazawa, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/763,735

(22) PCT Filed: Dec. 27, 1999

(86) PCT No.: PCT/JP99/07342

§ 371 (c)(1),
(2), (4) Date: Sep. 17, 2001

(87) PCT Pub. No.: WO00/42642

PCT Pub. Date: Jul. 20, 2000

(30) Foreign Application Priority Data

Jan. 11, 1999 (JP) ..................... 11-4288

(51) Int. Cl.
 *B23K 10/00* (2006.01)
 *B23K 26/00* (2006.01)
(52) U.S. Cl. .................. 219/121.43; 219/121.59; 219/121.41; 118/723 R; 438/714; 356/336
(58) Field of Classification Search ............. 219/121.4, 219/121.41, 121.44, 121.43, 121.59, 121.46; 118/723 R; 438/706–714; 386/336, 436; 315/431, 111.21
See application file for complete search history.

(56) References Cited

U.S. PATENT DOCUMENTS 6,355,570 B1 * 3/2002 Nakata et al. ............. 438/706
6,576,559 B2 * 6/2003 Nakata et al. ............. 438/706

FOREIGN PATENT DOCUMENTS

EP 0 837 315 4/1998

(Continued)

*Primary Examiner*—Mark Paschall
(74) *Attorney, Agent, or Firm*—Antonelli, Terry, Stout & Kraus, LLP.

(57) ABSTRACT

Making it possible to execute the detection of the particles floating inside a processing chamber with the use of an optical system including one observing window and one unit (An object of the present invention is, by using an optical system including one observing window and one unit, to make it possible to execute the detection of the particles floating inside a processing chamber.) Also, in order to be able to detect exceedingly feeble particle scattered-lights with a high-accuracy, when performing a desired thin-film forming or thin-film processing treatment toward a to-be-processed target inside the processing chamber, the following method is employed: First, the irradiation with a beam is executed into the processing chamber through the observing window. Here, the beam is P-polarized and is intensity-modulated with a frequency differing from an exciting source's frequency and its integer-multiples, and the observing window has an inclination that forms Brewster angle toward the P-polarized incident beam. Next, backward scattered-lights scattered by the particles inside the processing chamber are received and image-photographed at a detecting optical system through the above-described one and the same observing window. Moreover, the above-described frequency component and a wavelength component of the above-described intensity-modulated beam are detected out of the received signals. Finally, the detected components and the image-photographed image information are used so as to judge the number, the size, and the distribution of the particles.

11 Claims, 21 Drawing Sheets

U.S. PATENT DOCUMENTS

| | | |
|---|---|---|
| JP | 57-118630 | 7/1982 |
| JP | 58-9046 | 1/1983 |
| JP | 63-71633 | 4/1988 |
| JP | 3-25355 | 2/1991 |
| JP | 3-147317 | 6/1991 |
| JP | 6-82358 | 3/1994 |
| JP | 6-124902 | 5/1994 |
| JP | 7-318326 | 12/1995 |
| JP | 8-320294 | 12/1996 |
| JP | 9-243549 | 9/1997 |
| JP | 10-10036 | 1/1998 |
| JP | 10-213539 | 8/1998 |
| JP | 2000-193443 | 7/2000 |

\* cited by examiner (a)

(b)

(a)

(b)

(a)

(b)

- □ 0.2~0.4 μm
- ■ 0.4~0.6 μm
- ☐ 0.6~0.8 μm
- ■ 0.8 μm ≦

US 7,355,143 B1

CIRCUIT BOARD PRODUCTION METHOD AND ITS APPARATUS

TECHNICAL FIELD

The present invention relates to a method of producing a circuit board, such as a semiconductor board or a liquid crystal board, and an apparatus therefor. More particularly, it relates to a circuit board producing method and an apparatus therefor which are provided with a function of executing in-situ measurement of particles that float inside a processing chamber (vacuum processing chamber) for performing a thin-film formation (i.e., film deposition) or a processing such as a thin-film etching.

BACKGROUND ART

Plasma-utilizing processing apparatuses, the most typical of which is an etching apparatus, have been widely applied to a semiconductor producing process or a liquid crystal display's board producing process.

As one example of the plasma-utilizing processing apparatuses, there exists a parallel-plate type plasma etching apparatus illustrated in FIG. 26. In this type of apparatus, as illustrated in FIG. 26, the etching is performed as follows: An output voltage from a power amplifier 84 is modulated using a high-frequency signal from a signal generator 83. Next, the resultant high-frequency voltage is distributed by a distributor 85, then being applied between an upper electrode 81 and a lower electrode 82 which are located in parallel to each other inside a processing chamber. Moreover, the electrical discharge between both of the electrodes 81, 82 generates plasma 71 from an etching gas. Finally, a to-be-processed target, e.g., a semiconductor board (i.e., wafer), is etched by radicals of the plasma. As the high-frequency signal, there is employed a frequency of an order of, e.g., 400 kHz.

In the above-described plasma etching apparatus, there has been known the following fact: Reaction products produced as the result of the etching reaction by the plasma processing are deposited on the wall surface of the plasma processing chamber or on the electrodes. Then, the deposited products are flaked off with a lapse of time, thereby becoming floating particles. At the moment that the etching processing is over and the plasma discharge has been stopped, the floating particles drop down on the wafer, becoming the matters adhering thereto. The adhering matters give rise to a defect in the circuit characteristic or a defect in the circuit pattern's outside appearance, eventually becoming a cause of a decrease in the yield or a reduction in the reliability of the circuit components.

As apparatuses for inspecting the above-described particles that have adhered to the wafer surface, a lot of apparatuses have been reported and developed to practical use. In these apparatuses, however, the inspection is performed once the wafer has been extracted from the plasma processing apparatus. Accordingly, at a point in time when it was recognized that a large number of particles had been generated, another processing for the wafer had been already going on. This situation results in a problem of the decrease in the yield caused by the occurrence of a large number of defects. Also, in the estimation after the processing, it is impossible to determine the distribution and the time-elapsed variation of the generation of the particles inside the processing chamber.

Consequently, in the field of the semiconductor production and the liquid crystal display production, there exists a demand for a technology that allows an in-situ and real-time monitoring of the contamination situation inside the processing chamber.

The size of the particles floating inside the processing chamber is in the range of submicron to hundreds of μm. However, in the semiconductor production field where the higher integration is increasingly developing to a 256-Mbit DRAM (i.e., Dynamic Random Access Memory) and further up to a 1-Gbit DRAM, the minimum line-width of the circuit pattern is now becoming more and more microminiaturized, i.e., 0.25 μm to 0.18 μm. As a result, the size of the particles to be detected is also required to be of the submicron order.

As the prior arts for monitoring the particles floating inside the processing chamber (the vacuum processing chamber) such as the plasma processing chamber, the technologies disclosed in the following applications can be cited: JP-A-57-118630 (i.e., prior art 1), JP-A-3-25355 (i.e., prior art 2), JP-A-3-147317 (i.e., prior art 3), JP-A-6-82358 (i.e., prior art 4), JP-A-6-124902 (i.e., prior art 5), and JP-A-10-213539 (i.e., prior art 6).

In the above-described prior art 1, there is disclosed an evaporating apparatus including a member for irradiating a reaction space with a parallel light that has a spectrum differing from a spectrum of a self light-emitting light in the reaction space, and a member for detecting scattered-lights from microscopic particles generated in the reaction space as a result of receiving the irradiation with the parallel light.

Also, in the above-described prior art 2, there is disclosed a microscopic particle measuring apparatus for utilizing a scattering by a laser light so as to measure microscopic particles adhering to a semiconductor apparatus's board surface and floating microscopic particles, the microscopic particle measuring apparatus including a laser light phase modulating unit for generating two laser lights having an equal wavelength, having a phase difference therebetween, and modulated with a predetermined frequency, an optical system for causing the two laser lights to intersect to each other in a space containing the microscopic particles that are targets to be measured, a light detecting unit for receiving lights so as to convert the lights into electrical signals, the lights being obtained by scattering by the microscopic particles that are targets to be measured, and a signal processing unit for extracting, from among the electrical signals based on the scattered-lights, an electrical signal component the frequency of which is equal to or two times as large as the frequency of a phase modulating signal in the laser light phase modulating unit and the phase difference of which with the phase modulating signal is fixed in time.

Also, in the above-described prior art 3, there is described a technology including a step of performing a scanning irradiation with a coherent light so as to cause lights to be generated in situ, the lights being scattered inside a reaction container, and a step of detecting the lights scattered inside the reaction container, whereby the scatted lights are analyzed thereby measuring a contamination situation inside the reaction container.

Also, in the above-described prior art 4, there is described a particle detector including a laser member for generating a laser light, a scanner member for scanning, using the laser light, a region inside a reaction chamber of a plasma processing tool containing particles to be observed, a video camera for generating video signals of the laser lights scattered by the particles inside the region, and a member for processing and displaying an image of the video signals.

Also, in the above-described prior art 5, there is described a plasma processing apparatus including a camera apparatus for observing a plasma generating region inside a plasma processing chamber, a data processing unit for processing an image so as to obtain target information, the image being obtained by the camera apparatus, and a control unit for controlling at least one of an exhausting member, a process-gas introducing member, a high-frequency voltage applying member, and a purge-gas introducing member in accordance with the information obtained in the data processing unit so that the particles will be decreased.

Also, in the above-described prior art 6, there is described a microscopic particle censor including a light sending-out device for sending out a light beam with which a measurement volume is irradiated in a manner of being cut across, a detector, and the optical system that converges the scattered-lights from the measurement volume and directs the converged lights toward the light detector, the detector being configured so that the light detector generates a signal for indicating an intensity of the light directed toward the light detector, and a signal processing member including pulse detectors and an event detector, the pulse detectors connected to each other so that the pulse detectors analyze the signal from the light detector and detecting pulses within the signal from the light detector, the event detector corresponding to a microscopic particle and specifying a series of pulses caused by scattered-lights, the scattered-lights by the microscopic particle being associated with a plurality of irradiations with the light beam which are performed while the microscopic particle is moving within the measurement volume.

In the above-described respective prior arts, the irradiation with the laser light is performed from an observing window provided on a side wall of the plasma processing apparatus, and then a forward scattered laser light or a side scattered laser light is detected from an observing window that is provided on an opposed side wall or the other side wall and that differs from the above-described laser-irradiating observing window. Accordingly, in this method of detecting the forward scattered-light or the side scattered-light, the irradiating optical system and the detecting optical system are formed in different units each. Moreover, there is a need of providing the two observing windows on which these systems are mounted. Also, the optical-axis adjustment or the like must be made in either of the irradiating optical system and the detecting optical system. This has made the handling troublesome and complicated.

Also, the observing windows on the side wall of the processing chamber such as the plasma processing chamber are usually provided on almost all types of the processing apparatuses in order to monitor the plasma emitted-light and so on. In not a few cases, however, only one observing window is provided thereon. Consequently, there exists a problem that the conventional methods necessitating the two observing windows is inapplicable to the producing apparatuses having the processing chamber equipped with the only one observing window.

Furthermore, in the conventional methods of detecting the forward scattered-light or the side scattered-light, when trying to observe the particles-generated situation all over the entire surface of the to-be-processed target such as the wafer by performing a rotation scanning of the processing chamber-irradiating irradiation beam, many of the observing windows and the detecting optical systems become required. This condition becomes a cause of a tremendous amount of cost-up. In addition to this, providing many of the observing windows and the detecting optical systems is, actually, very difficult from the restriction on the space factor.

Meanwhile, in the semiconductor production field where the higher integration is increasingly developing to the 256-Mbit DRAM and further up to the 1-Gbit DRAM, the minimum line-width of the circuit pattern is now becoming more and more microminiaturized, i.e., 0.25 μm to 0.18 μm. As a result, the size of the particles to be detected is also required to be of the submicron order. In the prior arts, however, it is difficult to separate the particle scattered-lights from the plasma emitted-light. This condition limits the application of the prior arts into the observation of comparatively large particles, thereby making it difficult to detect the microscopic particles of the submicron order.

DISCLOSURE OF INVENTION

The present invention has been devised in view of the above-described points. Thus, an object of the present invention is, by co-using one observing window between the irradiating optical system and the detecting optical system, to permit an optical system including one unit to execute the detection of the particles floating inside the processing chamber. Also, another object of the present invention is to implement a high-reliability method and an apparatus therefor that allow the exceedingly feeble particle scattered-lights to be detected with a high-accuracy. Also, still another object of the present invention is to implement a method and an apparatus therefor that make it possible to judge the particles-generated situation all over the entire surface of the to-be-processed target such as the wafer.

In order to accomplish the above-described objects, in the present invention, when the to-be-processed target inside the processing chamber is subjected to, e.g., a desired thin-film forming or thin-film processing treatment, the following method is employed: First, the irradiation with a P-polarized laser beam having a predetermined wavelength is performed into the processing chamber through the observing window having an inclination that forms Brewster angle toward the P-polarized incident beam, the laser beam being intensity-modulated with a frequency differing from an exciting source's frequency and its integer-multiples. Next, backward scattered-lights scattered by the particles inside the processing chamber are received and image-photographed at the detecting optical system through the above-described one and the same observing window. Moreover, the above-described frequency component and a wavelength component of the above-described intensity-modulated beam are detected out of the received signals. Finally, the detected components and the image-photographed image information are used so as to judge the number, the size, and the distribution of the particles, then displaying the determined result on the display. Also, a rotation scanning of the into-processing chamber-irradiating irradiation beam is performed in the horizontal direction, thereby judging a 2-dimensional distribution of the particles.

BEST MODE FOR CARRYING OUT THE INVENTION

Hereinafter, using FIGS. 1 to 25, the explanation will be given concerning the embodiments of the present invention.

Incidentally, although, in the respective embodiments of the present invention described below, the examples applied to the parallel-plate type plasma etching apparatus used as the plasma dry etching apparatus will be presented, the application range of the present invention is not limited thereto. Namely, the present invention is applicable to the thin-film forming (i.e., film depositing) apparatuses such as a sputtering apparatus and a CVD apparatus, or to the various types of thin-film processing apparatuses such as an ECR etching apparatus, a microwave etching apparatus, and an ashing apparatus.

Figure 1:
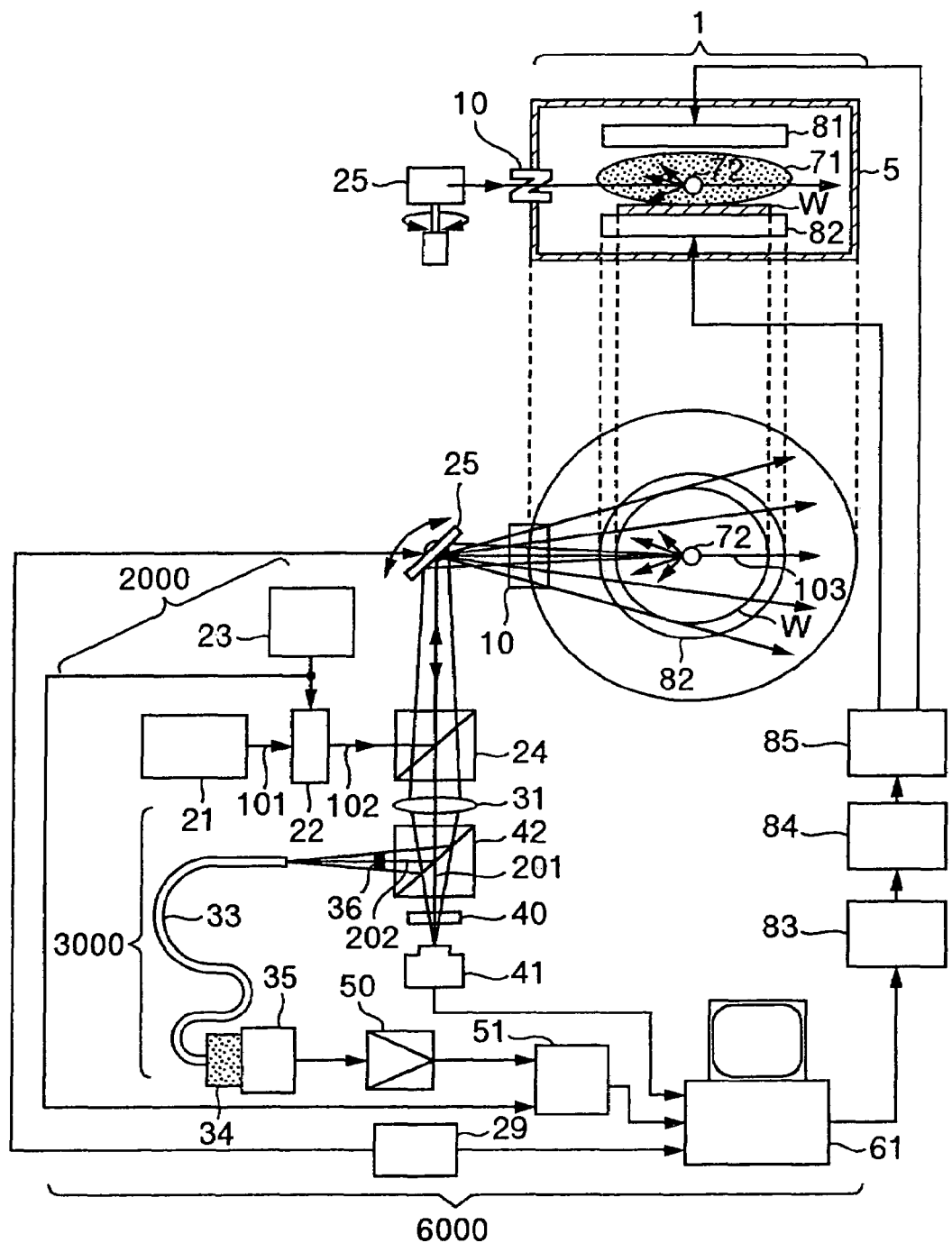
FIG. 1 is an explanatory diagram for illustrating the configuration of an etching processing apparatus having an in-plasma floating particle measuring apparatus relating to a first embodiment of the present invention.

First, based on FIGS. 1 to 8, the explanation will be given below concerning the plasma etching apparatus according to the 1st embodiment of the present invention. FIG. 1 is a diagram for illustrating the configuration of an etching processing apparatus 1 having an in-plasma floating particle measuring apparatus relating to the 1st embodiment of the present invention.

As illustrated in FIG. 1, in the etching processing apparatus 1, the etching is performed as follows: An output voltage from a power amplifier 84 is modulated using a high-frequency signal from a signal generator 83. Next, the resultant high-frequency voltage is distributed by a distributor 85, then being applied between an upper electrode 81 and a lower electrode 82 which are located in parallel to each other inside a processing chamber 5. Moreover, the electrical discharge between both of the electrodes 81, 82 generates plasma 71 from an etching gas. Finally, a to-be-processed target, i.e., a semiconductor board (wafer), is etched by radicals of the plasma. As the high-frequency signal, there is employed a frequency of an order of, e.g., 400 kHz.

The above-described in-plasma floating particle measuring apparatus basically includes a laser irradiating optical system 2000, a scattered-light detecting optical system 3000, and a signal processing system 6000. An irradiating light exit portion and a detected light entrance portion in the laser irradiating optical system 2000 and the scattered-light detecting optical system 3000 are located at an observing window 10 provided on a side wall of the processing chamber 5.

In the laser irradiating optical system 2000, at first, a P-polarized laser beam 101 emitted from a laser light source 21 (e.g., the 2nd harmonic YAG laser; the wavelength: 532 nm) is launched into an AO (Acousto-Optical) modulator 22. A rectangular wave signal with a frequency of, e.g., 170 kHz and a duty of, preferably, 58% is outputted from an oscillator 23 and is applied to the AO modulator 22, thereby intensity-modulating the laser beam (the S-polarized beam) 101 with the above-described frequency. Here, in the present embodiment where the high-frequency voltage applied between the electrodes inside the processing chamber 5 has been set to be 400 kHz, it is preferable to set the laser beam intensity-modulating frequency to be the above-described frequency of 170 kHz, which differs from 400 kHz and its harmonic components, i.e., 800 kHz, 1.2 MHz, . . . . The reason for this will be described later.

An intensity-modulated laser beam 102 is reflected by a polarization beam splitter 24 and a galvanometer mirror 25, thereby being introduced into the processing chamber 5 through the observing window 10 provided on the side wall of the processing chamber 5. Here, by rotating the galvanometer mirror 25 so as to scan the beam within a plane parallel to the wafer surface, it becomes possible to execute the particle detection all over the entire plane that is directly over the wafer.

Figure 2:
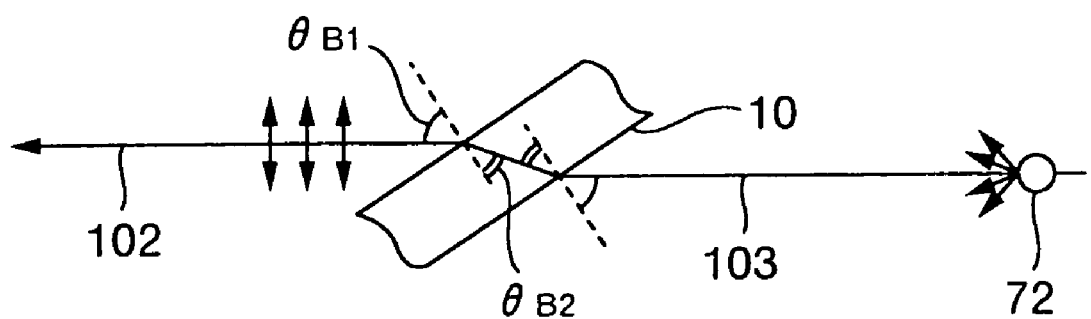
FIG. 2 is an explanatory diagram for illustrating an observing window and a laser light incident angle in the first embodiment of the present invention.
Figure 2:
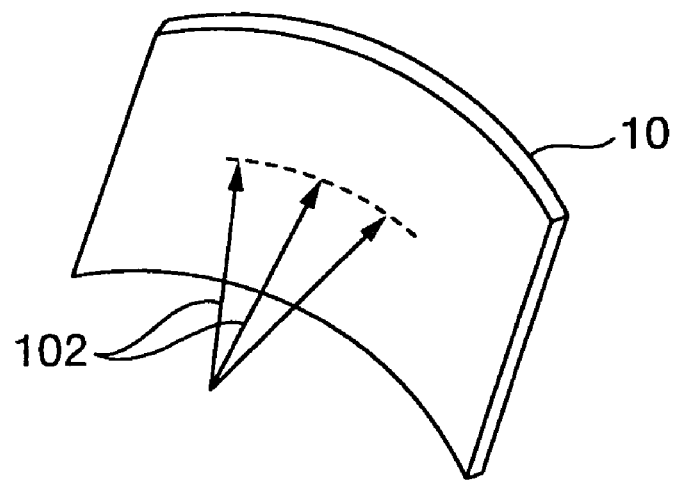

As illustrated in (a) in FIG. 2, the observing window 10 is provided with an inclination that forms Brewster angle $\theta_{B1}$ toward the P-polarized incident laser beam 102. As a result, the reflectance of the P-polarized incident laser beam 102 on this plane, theoretically, becomes equal to 0. Here, the Brewster angle $\theta_{B1}$ is represented by $\theta_{B1}=\tan^{-1}(n2/n1)$ (n1: the refractive index of the air, n2: the refractive index of a glass material of the observing window). Assuming that the laser wavelength is equal to 532 nm and the glass material of the observing window 10 is a synthesized silica (its refractive index at 532 nm is 1.46), it turns out that $\theta_{B1}$=55.60. Also, concerning $\theta_{B2}$, in much the same way, it turns out that $\theta_{B2}$=34.4°. Incidentally also, as illustrated in (b) in FIG. 2, the observing window 10 is formed in a warped configuration so that the observing window always maintain the same inclination toward the incident beam 102 while the rotation scanning of the incident beam 102 is being performed by the rotation of the galvanometer mirror 25.

A beam 103 introduced into the processing chamber 5 is scattered by floating particles 72 in the plasma. Out of the resultant particle scattered-lights, the backward scattered-lights propagating along the same optical-axis as that of the beam 103 pass through the observing window 10 and are reflected by the galvanometer mirror 25, then heading for the polarization beam splitter 24. Out of the backward scattered-lights, only the P-polarized components that will pass through the polarization beam splitter 24 are light-converged by an image-forming lens 31.

In order to specify the size and the generated position of the particles, the light-converged scattered-light is separated into two beams 201, 202 by a beam splitter 42. Then, the two beams are image-photographed or received by a CCD camera 41 and a bundle fiber 33, respectively.

Figure 3:
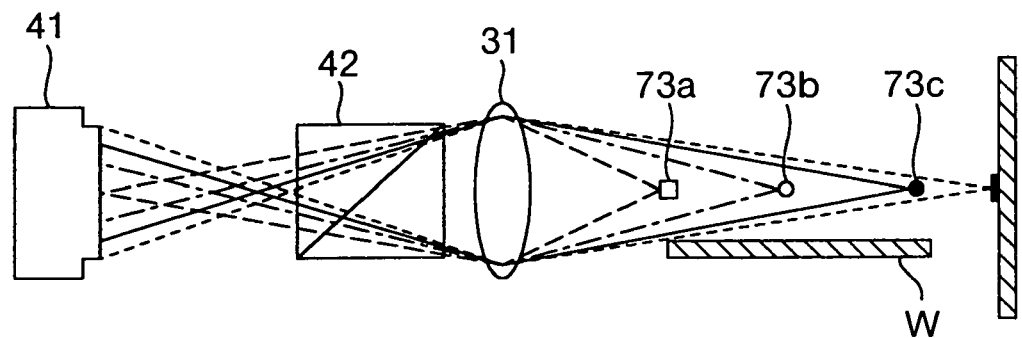
FIG. 3 is an explanatory diagram for illustrating a manner where the particle scattered-lights are image-photographed using a CCD camera in the first embodiment of the present invention.
Figure 3:
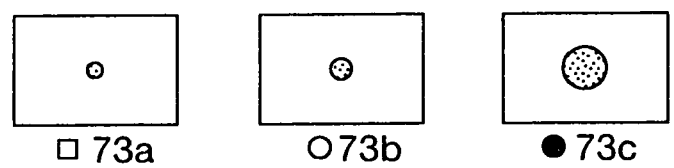

The beam 201 that has passed through the beam splitter 42 passes through an interference filter 40 having its pass-through central wavelength at the laser wavelength (i.e., 532 nm). Then, after the particle scattered-lights are wavelength-separated from the plasma emitted-light, the particle scattered-lights are image-photographed by the CCD camera 41. FIG. 3 is a diagram for illustrating a simplified manner where the scattered-lights are image-photographed using the CCD camera 41. As illustrated in (a) in FIG. 3, a wafer's front 73a and a light-incoming plane of the CCD camera 41 are in an image-forming relationship, and images of the scattered-lights from a wafer's center 73b and a wafer's back 73c are defocused. As a result, as illustrated in (b) in FIG. 3, the sizes of the images obtained from the scattered-lights scattered from one and the same particle differ from each other. Consequently, from the image-photographed images, information can be obtained which becomes a key to recognizing at which position the particle had been generated. It is impossible, however, to distinguish the particle from the other particles that are different in size. Accordingly, concerning the size of the particles, the judgement is made from the above-described image-photographed signals and signals obtained by a method explained next.

Figure 4:
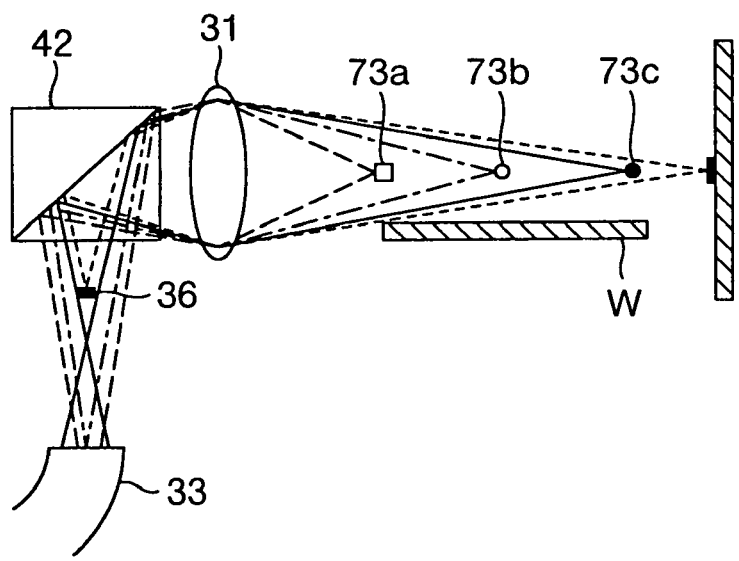
FIG. 4 is an explanatory diagram for illustrating a manner where the particle scattered-lights are received using a bundle fiber in the first embodiment of the present invention.

The beam 202 that has been reflected by the beam splitter 42 is light-converged onto a light-incoming plane of the bundle fiber 33 by the image-forming lens 31. As illustrated in FIG. 4, the wafer's center 73b and the light-incoming plane of the bundle fiber 33 are in an image-forming relationship. A fiber bundle region (i.e., light-receiving region) at the light-incoming end plane, however, is wide enough to be able to detect the defocused scattered-lights from the wafer's both ends 73a, 73c. Consequently, it is possible to detect, with an equal-sensitivity, the particle backward scattered-lights from the wafer's front to the wafer's back. Also, the scattered-lights generated at the inside-wall of the processing chamber 5 are image-formed before the light-receiving plane of the bundle fiber 33, and accordingly a space filter 36 is installed at the image-forming position so as to light-shield the scattered-lights. A light-emitting end of the bundle fiber 33 is connected to a spectroscope 34 such as a monochrometer or an interference filter set to be the laser wavelength. After the particle scattered-lights are wavelength-separated from the plasma emitted-light, the particle scattered-lights are photoelectrically converted by a photoelectric converter 35.

The photoelectrically converted signals, after being amplified by an amplifier 50 having a bandwidth that is sufficiently broader than the laser beam intensity-modulating frequency, are synchronously detected by a lock-in amplifier 51. This extracts, from the converted signals, particle scattered-light components having the frequency of 170 kHz. The above-described synchronous detection is performed employing, as the reference signal, the 170 kHz frequency and 50% duty of rectangular wave signal outputted from the oscillator 23 that is used for intensity-modulating the laser beam.

Figure 5:
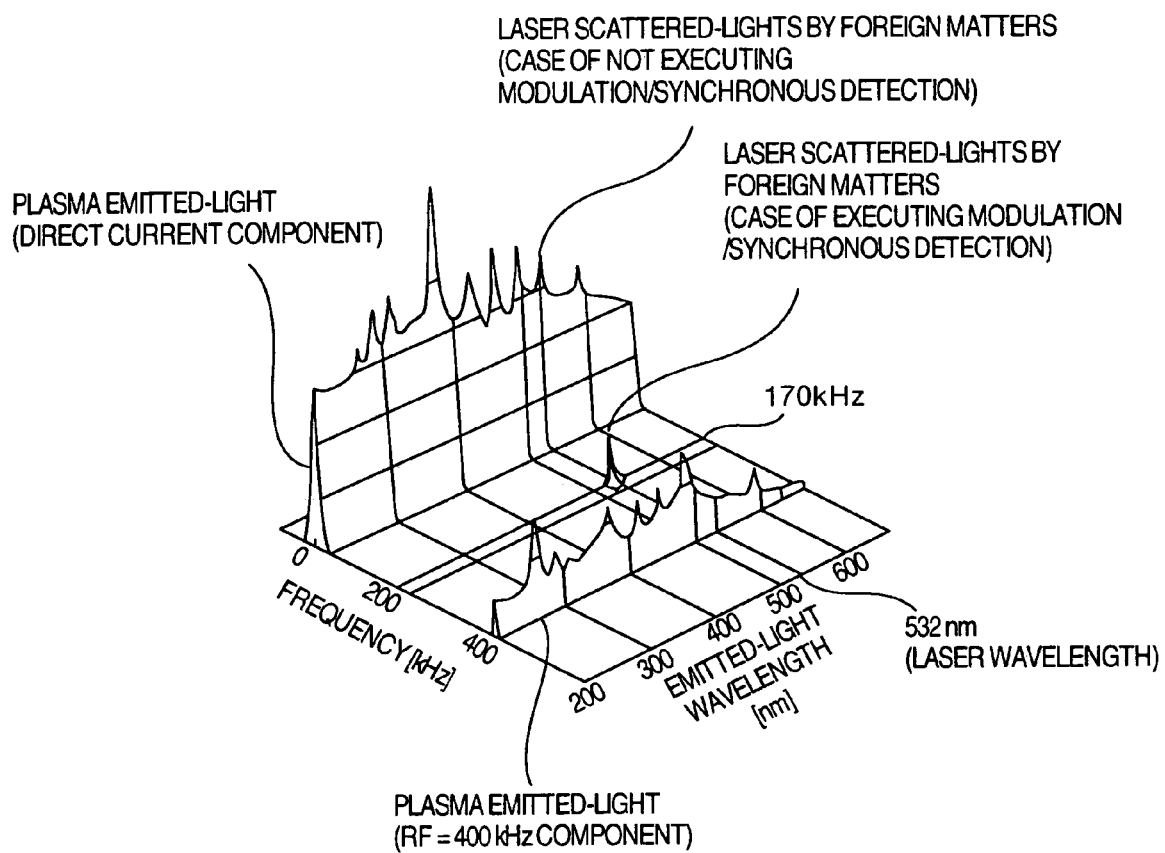
FIG. 5 is an explanatory diagram for illustrating a manner of the wavelength/frequency-separation of the particle scattered-lights from the plasma emitted-light in the first embodiment of the present invention.

An experiment made by the present inventor et al. has verified that the intensity of the plasma emitted-light is in synchronization with the plasma exciting frequency. As illustrated in FIG. 5, the particle signals are separated from the plasma emitted-light in the two regions of the wavelength and the frequency, then being detected. Here, the particle signals have been obtained by wavelength-separating the particle scattered-lights from the plasma emitted-light and by intensity-modulating and synchronously detecting the scattered-lights with the above-described frequency of 170 kHz that differs from the plasma exciting frequency and its integer-multiples. The present inventor et al. have confirmed experimentally that this intensity-modulation/synchronous detection method allows the exceedingly feeble particle scattered-lights to be detected from the plasma emitted-light with a high-sensitivity.

Namely, as illustrated in FIG. 5, although the plasma emitted-light is distributed continuously in the wavelength region, in the frequency region, the plasma emitted-light exists in a discrete manner and thus empty areas are found to exist in the frequency region. Consequently, the following method makes it possible to detect the scattered-lights from the particles in a state of being separated from the plasma emitted-light: For example, the laser light with the wavelength of 532 nm is intensity-modulated with a frequency of, e.g., 170 kHz which differs from the above-described plasma emitting frequency, and is launched into the plasma processing chamber, and out of the detected light, only a 532 nm wavelength and 170 kHz frequency of component, i.e., only a peak signal, is extracted. Incidentally, the peak signal based on the conventional methods has become difficult to distinguish from the plasma emitted-light.

In this way, the present embodiment substantially eliminates the influences of the reflected-lights from the observing window's surface and the processing chamber inside-wall scattered-lights, which are likely to become loud noises in the detection of the backward scattered-lights. Moreover, in the present embodiment, the above-described intensity-modulation/synchronous detection method allows the exceedingly feeble particle scattered-lights to be detected with a high-sensitivity from the plasma emitted-light noise that becomes a problem in the detection of the in-plasma particles. Also, the employment of the detection of the backward scattered-lights makes it possible to configure, as one unit, the laser irradiating optical system and the scattered-light detecting optical system, thereby making the present embodiment applicable to the processing apparatus equipped with the only one observing window 10. Furthermore, the optical-axis adjustment and the like become easier in comparison with the processing apparatus where the laser irradiating optical system and the scattered-light detecting optical system are separated from each other. As a consequence, its optical system in total becomes compact.

Figure 6:
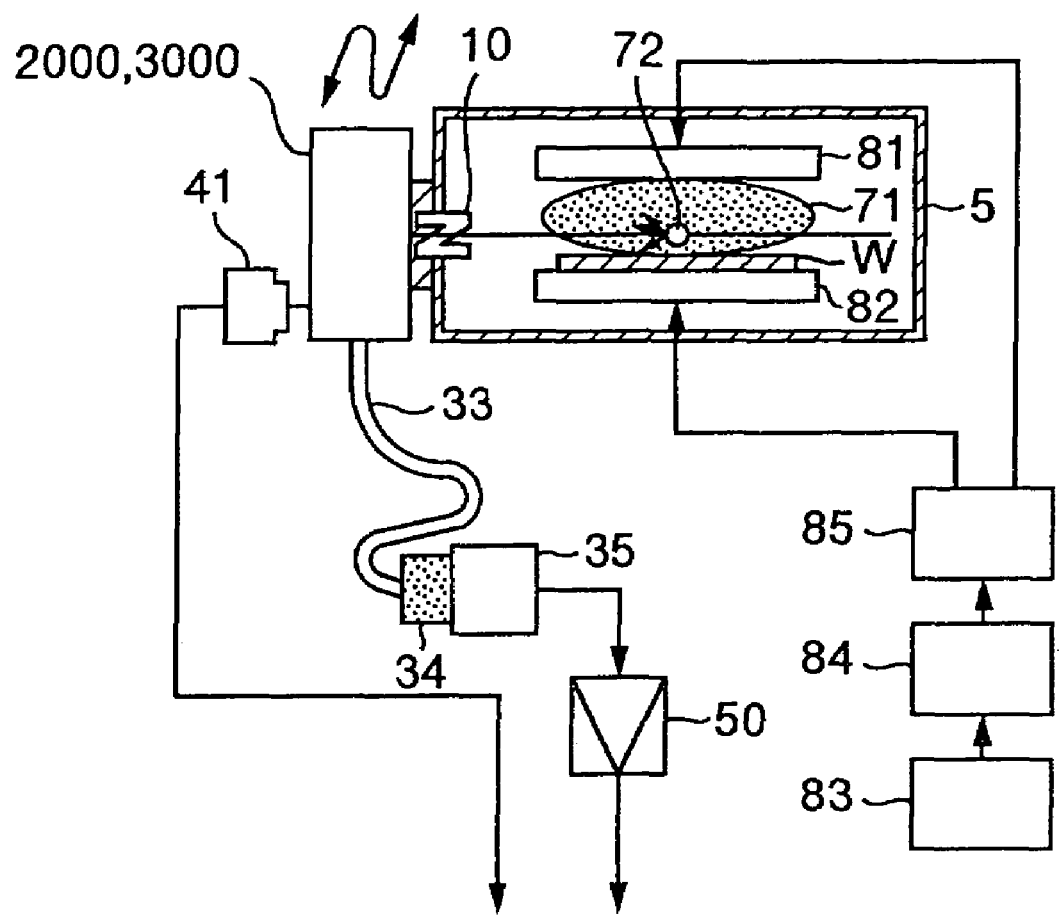
FIG. 6 is an explanatory diagram for illustrating a sliding function of an irradiating/detecting optical system in the in-plasma floating particle measuring apparatus in the first embodiment of the present invention.
Figure 7:
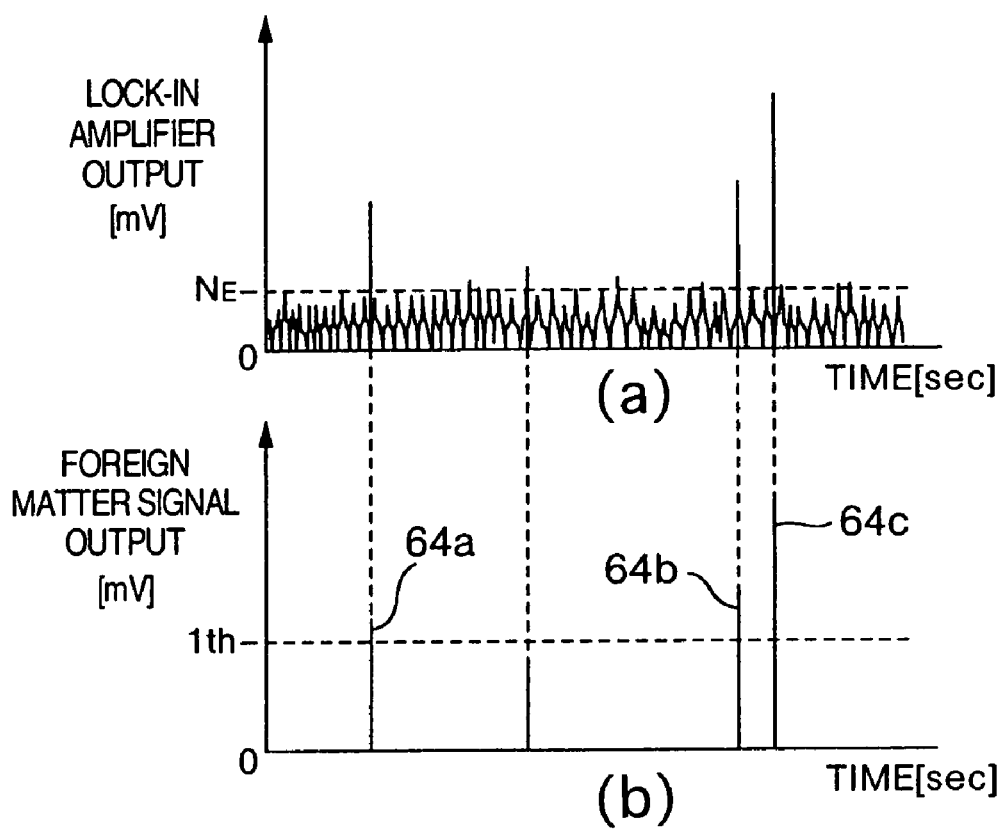
FIG. 7 are explanatory diagrams for illustrating detected signals, the signals after the threshold value processing, and the displayed example onto the display in the first embodiment of the present invention.
Figure 7:
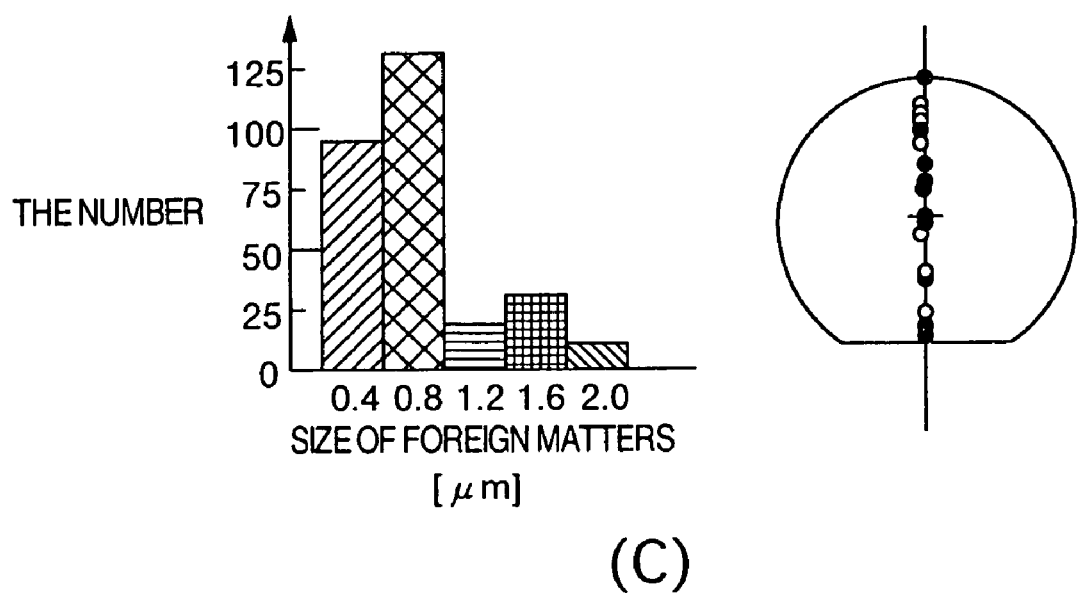

Here, although it is said that many of the floating particles exist on a plasma sheath interface, the position of the plasma sheath interface differs depending on the electrodes' spacing and so on. In addition, the floating particles exist elsewhere other than the plasma sheath interface. Thus, as illustrated in FIG. 6, the laser irradiating optical system 2000 and the scattered-light detecting optical system 3000, which are configured as one unit, are configured so that they are able to slide up and down in an oblique direction, i.e., in parallel to the above-described inclination of the observing window 10. The employment of the configuration like this allows the particles to be detected at different height regions in the plasma.

The outputs from the lock-in amplifier 51 are sent to a computer 61. The computer 61 displays the fetched signals in sequence on the display in such a manner as to be illustrated in, e.g., (a) in FIG. 7. Here, the detected signals contain electrical noises NE that are generated in the amplifier 50, the lock-in amplifier 51, and so on. Consequently, the threshold value processing is performed at the time of the display and, as illustrated in (b) in FIG. 7, the signals smaller than NE are set to be 0 mv and only the signals that are larger than NE are displayed. This makes it easy to judge the particle signals.

In the signal processing system 6000, concerning the size, the number, and the position of the generated particles, the judgement is made from the obtained particle signal intensity and the image-photographed images by the CCD camera 41. Thus, regarding the image-photographed images by the CCD camera 41, a threshold value I th is established toward the lock-in amplifier output. Moreover, only when the signal intensity exceeds the threshold value I th, the particle is assumed to be generated, then recording the image.

Next, in the computer 61, the signal intensity and the image-photographed image data for a particle diameter obtained in advance by the experiment are compared with the detected particle signal intensity and image-photographed images. Based on the comparison, the computer 61 judges the size, the number, and the position of the generated particles, then displaying the result on the display in such a manner as to be illustrated in, e.g., (c) in FIG. 7.

Figure 8:
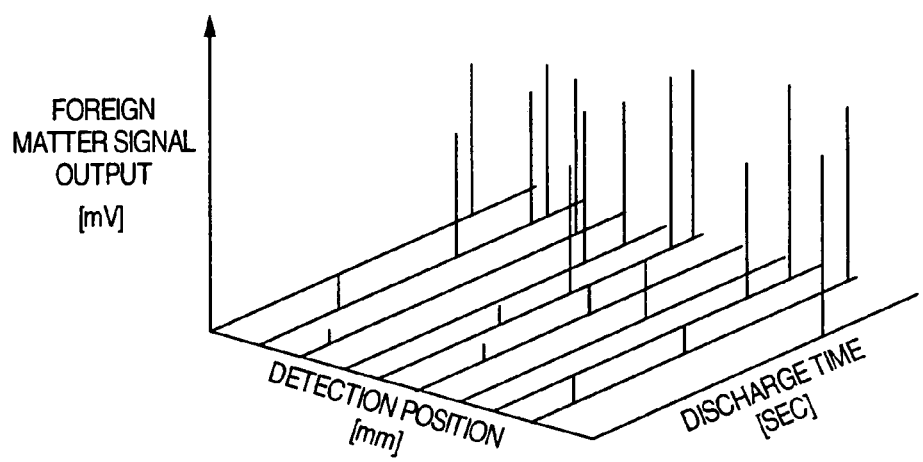
FIG. 8 are explanatory diagrams for illustrating the detected signals, the size and the number of the generated particles, and a displayed example of the 2-dimensional distribution of the particles.
Figure 8:
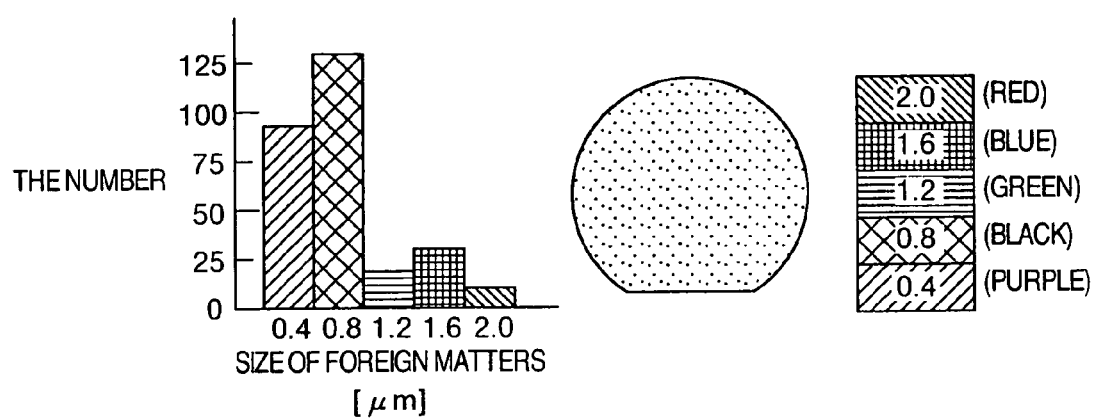

Here, in the present embodiment, the configuration has been employed where the galvanometer mirror 25 makes it possible to scan the beam all over the entire surface of the wafer. Thus, the computer 61 sends a scanning signal to the galvanometer mirror 25 through a galvano driver 29 and, while thereby scanning the beam, the computer fetches the particle signal and the image-photographed image at each scanning position in synchronization with the galvanometer mirror's operation. This makes it possible to grasp and recognize, as illustrated in FIG. 8, the 2-dimensional distribution of the particles on the wafer in addition to the particles-generated positions on the wafer's front and back.

Also, the computer 61 counts the number of the generated particles, thereby judging the contamination situation inside the processing chamber. If the total number of the generated particles is found to exceed a predetermined reference value, the computer 61 terminates the etching processing. Moreover, using an alarm or the like, the computer 61 informs the operator of the information to the effect, which permits the operator to perform an operation, such as cleaning of the processing chamber, in accordance with the information.

As having been described so far, the present embodiment substantially eliminates the influences of the reflected-lights from the observing window's surface and the processing chamber inside-wall scattered-lights, which are likely to become loud noises in the detection of the backward scattered-lights. Moreover, in the present embodiment, the above-described intensity-modulation/synchronous detection method allows the exceedingly feeble particle scattered-lights to be detected in a state of being separated from the plasma emitted-light noise that becomes a problem in the detection of the in-plasma particles. This enhances the detection sensitivity, thereby making it possible to detect the microscopic particles of the submicron order which are expected to be difficult to detect using the conventional methods.

Also, the present embodiment allows the exceedingly feeble particle scattered-lights to be detected in a state of being separated from the plasma emitted-light in the two regions of the wavelength and the frequency. Accordingly, as compared with the conventional methods of performing the wavelength-separation alone, the present embodiment results in an effect of tremendously enhancing the detection sensitivity for the in-plasma floating particles. The minimum detection sensitivity obtainable in the conventional case of the wavelength-separation alone has been limited to, at most, an order of $\phi 1$ $\mu$m. In contrast to this, the method according to the present invention makes it possible to enhance the detection sensitivity up to $\phi 0.2$ $\mu$m, thereby bringing about an effect of allowing a stable detection of the particles all over the entire surface of the wafer. Incidentally, the laser wavelength is changed to a shorter wavelength in order to increase the scattered-intensity, the laser output is switched to a higher output, or changing to the shorter wavelength and switching to the higher output are executed simultaneously. This operation makes it possible to enhance the detection sensitivity even further.

Also, in the present embodiment, the employment of the detection of the backward scattered-lights permits the irradiating optical system and the detecting optical system to be configured as one unit, thereby making it possible to configure the particle detecting apparatus that is small-sized and is easy to mount and adjust. Also, the employment of the detection of the backward scattered-lights permits the rotation scanning of the irradiating beam to be executed in the horizontal direction, thereby making it possible to easily grasp and recognize the 2-dimensional distribution of the particles.

Moreover, in the present embodiment, the configuration is employed where the irradiating/detecting optical system is able to be slid up and down in the oblique direction. This condition makes it possible to observe the different plasma regions and to recognize the distribution of the particles in the up-and-down direction. At this time, since the irradiating optical system and the detecting optical system have been configured as one unit, the sliding causes no shift of the irradiating/detecting optical-axis and thus there is no need of the readjustment.

Furthermore, according to present embodiment, the detection of the particles is executed all over the entire surface of the wafer so as to judge the number, the size, and the distribution of the particles. This permits the operator to confirm the information in real time on the display.

Also, according to present embodiment, based on the information about the number, the size, and the distribution of the generated particles, it is possible to judge the contamination situation inside the processing chamber in real time. This condition not only accomplishes the optimization at the timing for the cleaning so as to enhance the throughput, but also prevents the occurrence of the mass defects (i.e., the occurrence of a large quantity of defects at a time) so as to enhance the yield. Also, it is possible to proceed the processing while monitoring all the time the number of the particles inside the processing chamber. As a result, the semiconductor board and the liquid crystal board manufactured in this way turn out to become high-quality and high-reliability products that are manufactured in an environment containing only the particles the number of which is smaller than a reference value.

Also, according to present embodiment, there exist no necessities for the contamination situation judgement on the processing chamber with the use of a dummy wafer and the contamination situation judgement based on an extraction inspection. This condition brings about a cost reduction in the dummy wafer and the enhancement in the throughput.

Next, based on FIGS. 9, 10, the explanation will be given below concerning the 2nd embodiment of the present invention.

Figure 9:
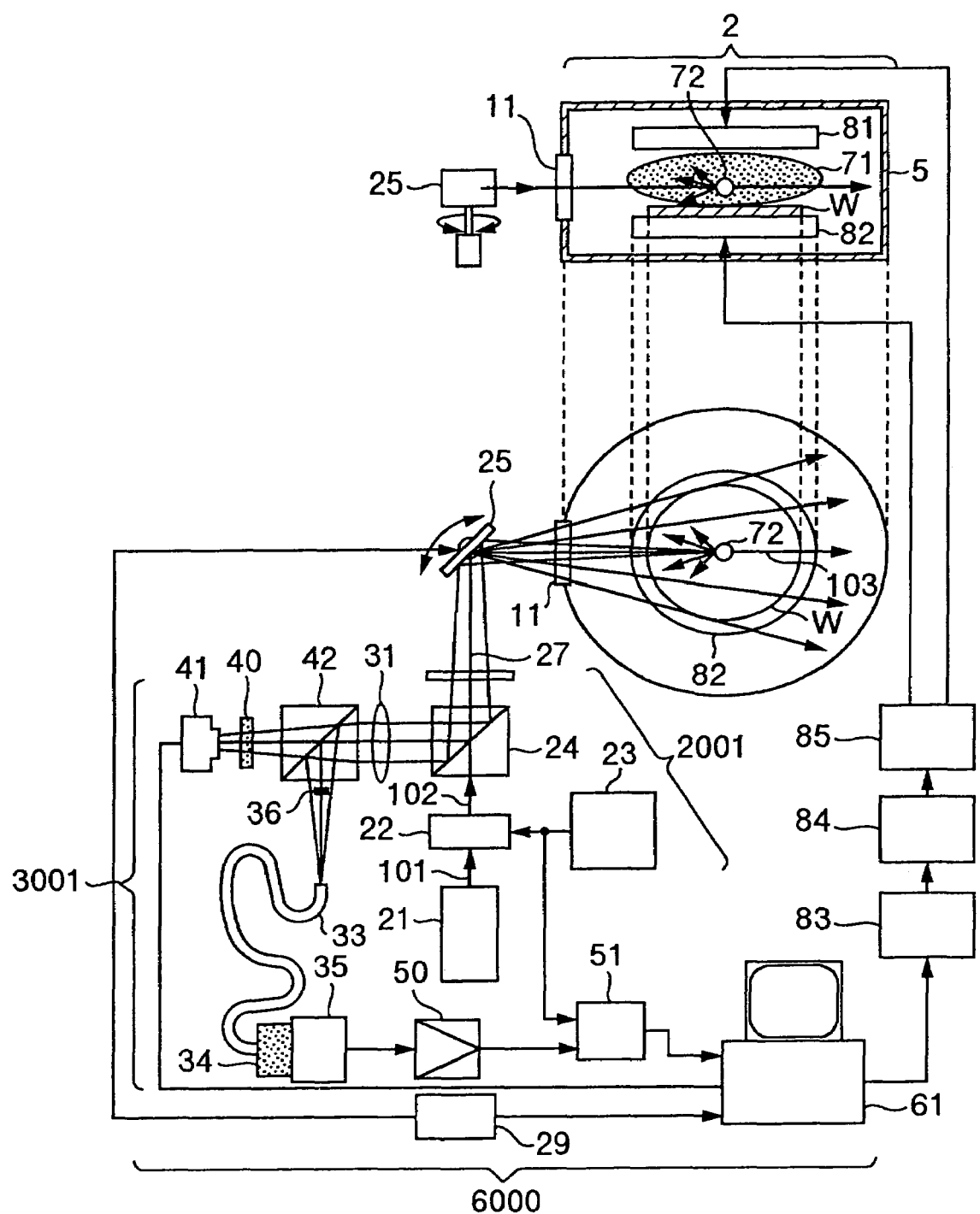
FIG. 9 is an explanatory diagram for illustrating the configuration of an etching processing apparatus having an in-plasma floating particle measuring apparatus relating to a second embodiment of the present invention.
Figure 10:
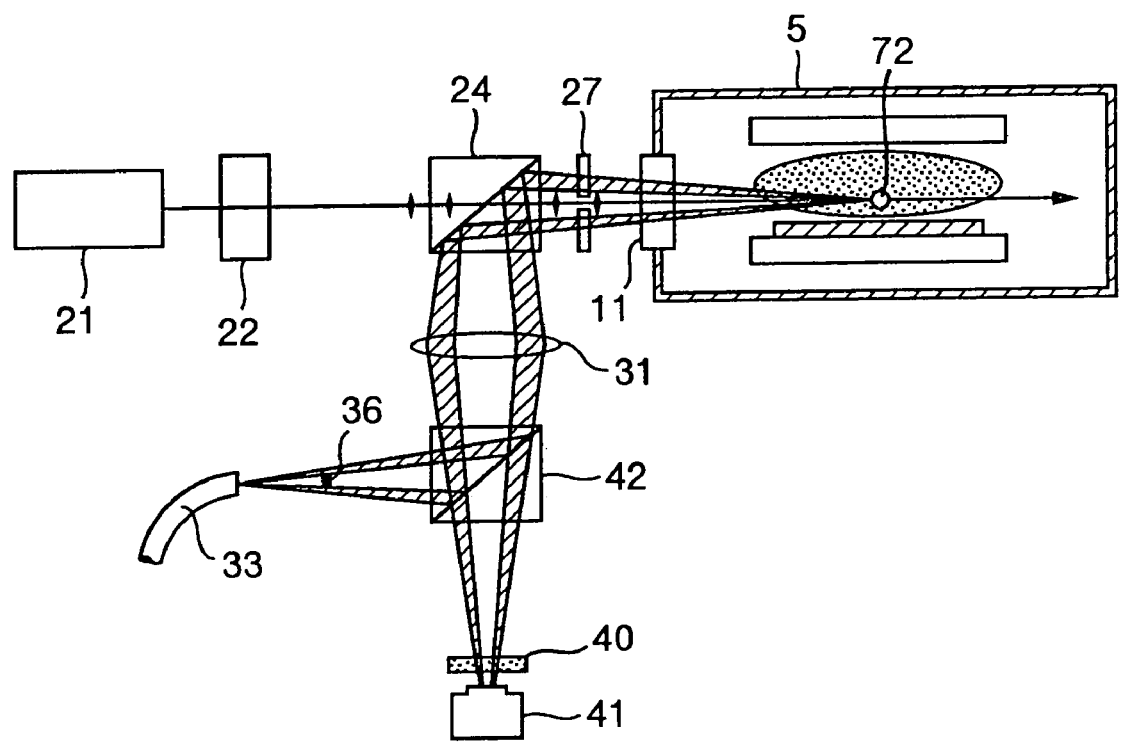
FIG. 10 is an explanatory diagram for illustrating an optical system for detecting the particle scattered-lights in the second embodiment of the present invention.

FIG. 9 is a diagram for illustrating the configuration of an etching processing apparatus 2 having an in-plasma floating particle measuring apparatus relating to the present 2nd embodiment.

With respect to the in-plasma floating particle measuring apparatus in the present embodiment, the case is assumed where, in order to detect the plasma emitted-light or the like, the measuring apparatus is mounted on the etching processing apparatus that has been already equipped with an observing window 11. Namely, the present embodiment is about the in-plasma floating particle measuring apparatus that is also effective in the case of the etching processing apparatus that has none of such a special structure as providing the observing window with the Brewster angle, i.e., in the case where a large amount of reflected-lights are generated from the observing window's surface.

In the present embodiment, an irradiating/detecting optical system of the in-plasma floating particle measuring apparatus is mounted on the etching processing apparatus by employing a method, such as attaching an attachment like a base plate in proximity to the observing window 11 and mounting the irradiating/detecting optical system through the attachment. In addition, as is the case with the above-described 1st embodiment, the irradiating/detecting optical system is configured so that the optical system is able to be slid in an up-and-down direction on the attachment and thus it is possible to detect the particles at the different height of plasma regions.

Also, in the above-described 1st embodiment, the configuration has been employed where the irradiation with the P-polarized light is performed and, out of the particle scattered-lights, the S-polarized components perpendicular to the irradiating light are detected. In general, however, the scattered-lights are intense in the same polarization direction as that of the incident light. Thus, in the present embodiment, the configuration is implemented where the components having the same polarization direction as that of the incident light are extracted. Also, unlike the above-described 1st embodiment, the polarization state of the incident light into the observing window is not limited to the P-polarized light.

Since the plasma processing chamber and the processing method are the same as those in the above-described 1st embodiment, the explanation thereof will be omitted. Also, as is the case with the above-described 1st embodiment, the technology of the intensity-modulation/synchronous detection is used, and the particle scattered-lights are detected in a state of being separated from the plasma emitted-light in the two regions of the wavelength and the frequency, and the processing chamber inside-wall scattered-lights are light-shielded by a space filter.

The in-plasma floating particle measuring apparatus in the present embodiment basically includes a laser irradiating optical system 2001, a scattered-light detecting optical system 3001, and a signal processing system 6000. Since the signal processing system 6000 is the same as that in the above-described 1st embodiment, the explanation thereof will be omitted.

In the present 2nd embodiment, an intensity-modulated P-polarized beam 102 passes through a polarization beam splitter 24, then passing through a slit portion of a ½th-wavelength plate 27 equipped with the slit portion. After that, the P-polarized beam 102 is reflected by a galvanometer mirror 25, then being introduced into a processing chamber 5 through the observing window 11. The slit direction of the ½th-wavelength plate 27 is a direction illustrated in FIG. 10 for illustrating a simplified optical path of the reflected-lights from the observing window and a simplified manner where the scattered-lights are received.

The backward scattered-lights generated by floating particles 72 in plasma 71 pass through the observing window 11 and are reflected by the galvanometer mirror 25, then heading for the ½th-wavelength plate 27. Out of the backward scattered-lights, the scattered-lights having passed through the ½th-wavelength plate 27, which are indicated by a sloped line in FIG. 10, are rotated by 90° in the polarization direction and become S-polarized lights. As a result, the resultant S-polarized scattered-lights are reflected by the polarization beam splitter 24, thereby being detected by the scattered-light detecting optical system. Meanwhile, the directly reflected-lights from the surface and the rear surface of the observing window 11 pass through the slit portion of the ½th-wavelength plate 27. As a result, the directly reflected-lights remain P-polarized and passes through the polarization beam splitter 24, thus being never detected by the scattered-light detecting optical system.

Here, a laser-incoming side of the observing window 11 is subjected to an anti-reflection coating that causes the reflectance to become its minimum toward the wavelength, the polarization state, and the incident angle of the incident beam. This makes it possible to reduce the reflected-lights. Since the light-reception and the image-photographing of the scattered-lights are the same as those in the above-described 1st embodiment, the explanation thereof will be omitted.

A computer 61 is provided with a terminal for outputting the obtained result to the plasma processing apparatus and so on, and is provided with an input terminal for obtaining operating information such as cumulative discharge time from the plasma processing apparatus. As is the case with the 1st embodiment, based on the information obtained from the in-plasma floating particle measuring apparatus, the computer 61 is able to monitor and control the plasma processing apparatus.

In this way, the present embodiment makes it possible to obtain the same effects as those of the 1st embodiment. Furthermore, even if the observing window having no special structure generates the reflected-lights, the present embodiment permits the particle scattered-lights to be detected without being subjected to the influences of the reflected-lights.

Also, the present embodiment makes it possible to detect the particle scattered-lights having the same polarization direction as that of the irradiating light, thereby allowing the particle scattered-signals to be detected more efficiently.

Next, based on FIGS. 11, 12, the explanation will be given below concerning the 3rd embodiment of the present invention.

Figure 11:
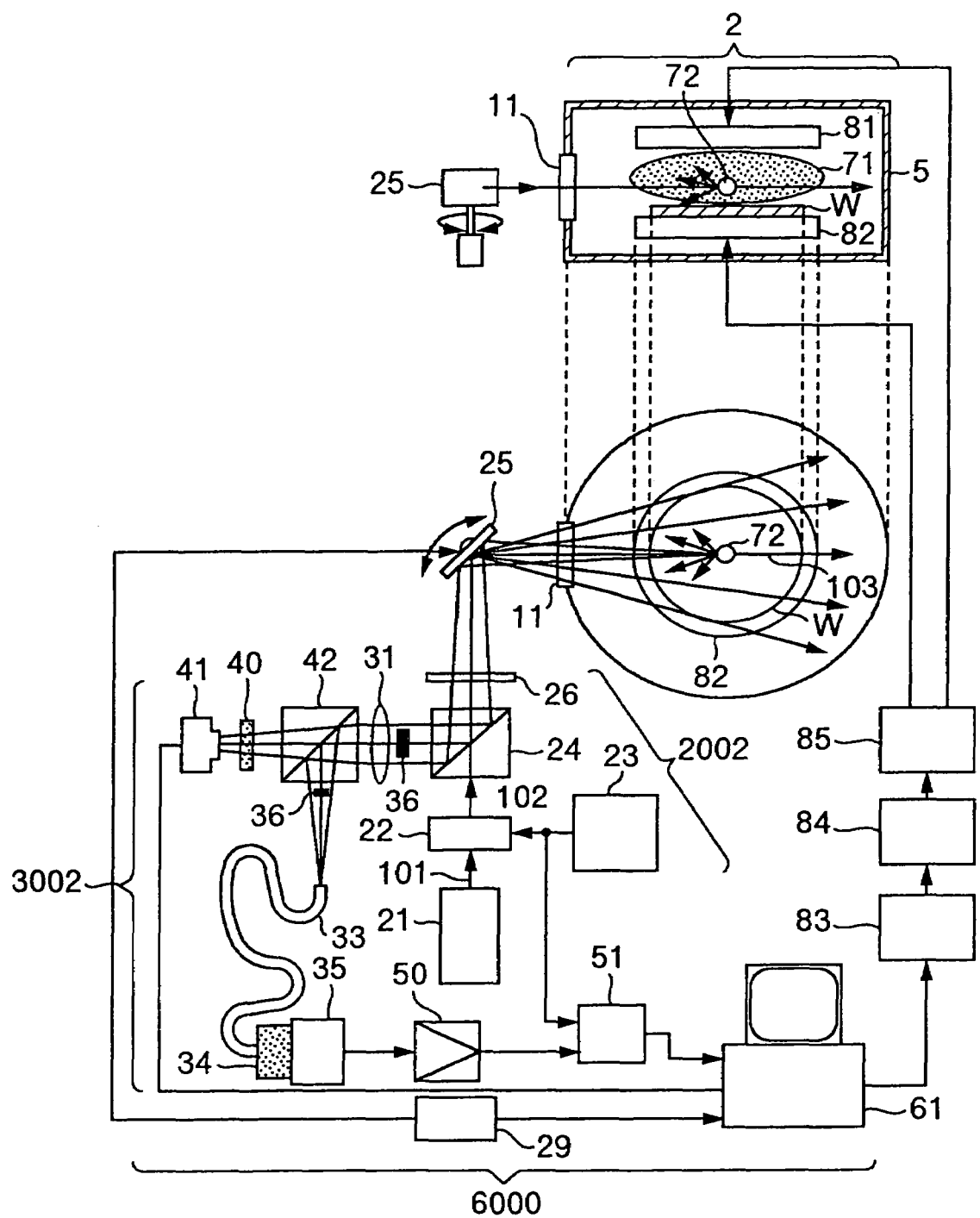
FIG. 11 is an explanatory diagram for illustrating the configuration of an etching processing apparatus having an in-plasma floating particle measuring apparatus relating to a third embodiment of the present invention.

FIG. 11 is a diagram for illustrating the configuration of an etching processing apparatus 2 having an in-plasma floating particle measuring apparatus relating to the present 3rd embodiment.

With respect to the in-plasma floating particle measuring apparatus in the present embodiment, as is the case with the above-described 2nd embodiment, the case is assumed where, in order to detect the plasma emitted-light or the like, the measuring apparatus is mounted on the etching processing apparatus that has been already equipped with an observing window 11. Namely, the present embodiment is about the in-plasma floating particle measuring apparatus that is also effective in the case of the etching processing apparatus that has none of such a special structure as providing the observing window with the Brewster angle, i.e., in the case where there exist the reflected-lights from the observing window's surface.

In the present embodiment, as is the case with the above-described 2nd embodiment, an irradiating/detecting optical system of the in-plasma floating particle measuring apparatus is mounted on the etching processing apparatus by employing a method, such as attaching an attachment like a base plate in proximity to the observing window 11 and mounting the irradiating/detecting optical system through the attachment. In addition, as is the case with the above-described 1st embodiment, the irradiating/detecting optical system is configured so that the optical system is able to be slid in an up-and-down direction on the attachment and thus it is possible to detect the particles at the different height of plasma regions.

The present embodiment differs from the above-described 2nd embodiment in a point of executing a circularly-polarized irradiation/circularly-polarized detection.

Since the plasma processing chamber and the processing method are the same as those in the above-described 1st embodiment, the explanation thereof will be omitted. Also, as is the case with the above-described 1st embodiment, the technology of the intensity-modulation/synchronous detection is used, and the particle scattered-lights are detected in a state of being separated from the plasma emitted-light in the two regions of the wavelength and the frequency, and the plasma processing chamber inside-wall scattered-lights are light-shielded by a space filter.

The in-plasma floating particle measuring apparatus in the present embodiment basically includes a laser irradiating optical system 2002, a scattered-light detecting optical system 3002, and a signal processing system 6000. Since the signal processing system 6000 is the same as that in the above-described 1st embodiment, the explanation thereof will be omitted.

As is the case with the above-described 1st and 2nd embodiments, an intensity-modulated P-polarized beam 102 passes through a polarization beam splitter 24, and a ¼th-wavelength plate 26, thereby becoming a circularly-polarized beam 104. After that, the circularly-polarized beam 104 is reflected by a galvanometer mirror 25, then being introduced into a processing chamber 5 through an observing window 11.

Figure 12:
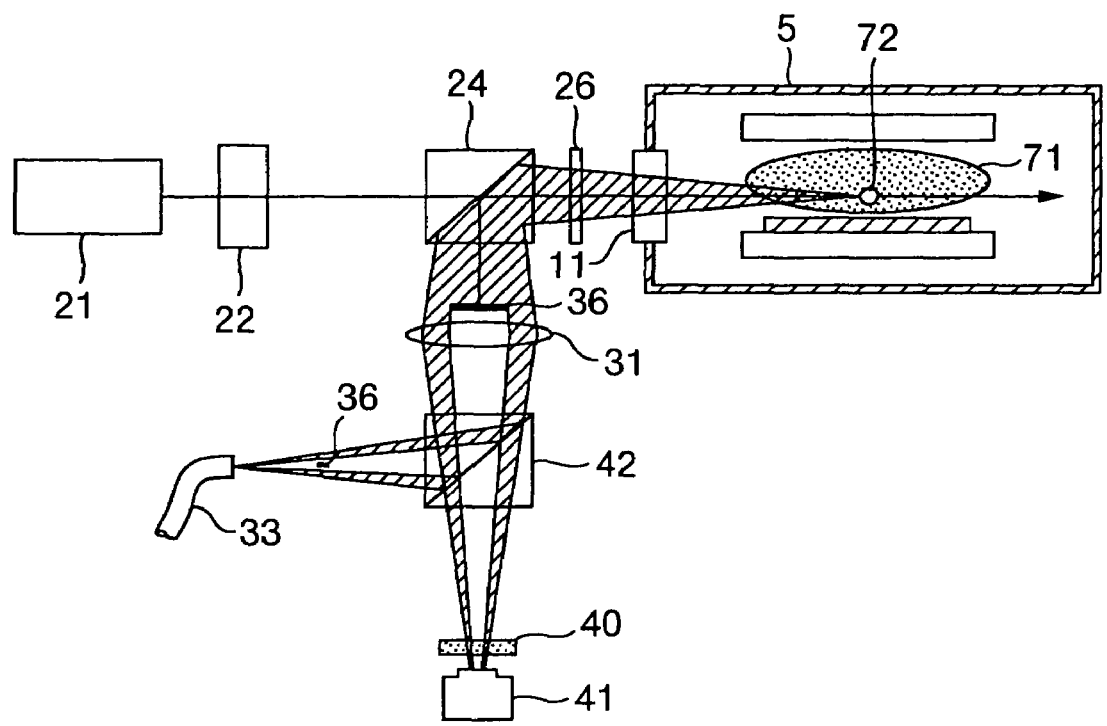
FIG. 12 is an explanatory diagram for illustrating an optical system for detecting the particle scattered-lights in the third embodiment of the present invention.

FIG. 12 is a diagram for illustrating a simplified optical path of the reflected-lights from the observing window and a simplified manner where the scattered-lights are received.

As illustrated in FIGS. 11, 12, the backward scattered-lights generated by floating particles 72 in plasma 71 pass through the observing window 11 and are reflected by the galvanometer mirror 25, then heading for the ¼th-wavelength plate 26. The scattered-lights having passed through the ¼th-wavelength plate 26 again are rotated by 90° in the polarization direction and become S-polarized lights. As a result, the resultant S-polarized scattered-lights are reflected by the polarization beam splitter 24, thereby being detected by the scattered-light detecting optical system. Meanwhile, the directly reflected-lights from the surface and the rear surface of the observing window also pass through the ¼th-wavelength plate 26, thereby becoming S-polarized lights. As a result, the resultant S-polarized reflected-lights are reflected by the polarization beam splitter 24, thereby heading for the scattered-light detecting optical system. Accordingly, a space filter 36 is installed before or behind an image-forming lens 31 so as to light-shield the observing window reflected-lights.

Here, as is the case with the above-described 1st and 2nd embodiments, a laser-incoming side of the observing window 11 is subjected to an anti-reflection coating 15 that causes the reflectance to become its minimum toward the wavelength and the incident angle of the incident beam. This allows the reflected-lights to be reduced.

In this way, in the present embodiment, the circularly-polarized irradiation/circularly-polarized detection makes it possible to configure the in-plasma floating particle measuring apparatus that is the same as that of the 2nd embodiment.

Also, in the present embodiment as well, as is the case with the 2nd embodiment, there are provided with a terminal for outputting the result obtained by the signal processing system to the plasma processing apparatus and so on, and an input terminal for obtaining operating information such as cumulative discharge time from the plasma processing apparatus. This condition permits the in-plasma floating particle measuring apparatus to monitor and control the plasma processing apparatus.

In this way, as is the case with the 2nd embodiment, even if the observing window having no special structure generates the reflected-lights, the present embodiment permits the particle scattered-lights to be detected by the circularly-polarized irradiation/circularly-polarized detection without being subjected to the influences of the reflected-lights.

Also, the present embodiment executes the circularly-polarized irradiation/circularly-polarized detection, thereby allowing the particle scattered-signals to be detected more efficiently as compared with the 1st embodiment.

Next, based on FIGS. 13, 14, the explanation will be given below concerning the 4th embodiment of the present invention.

Figure 13:
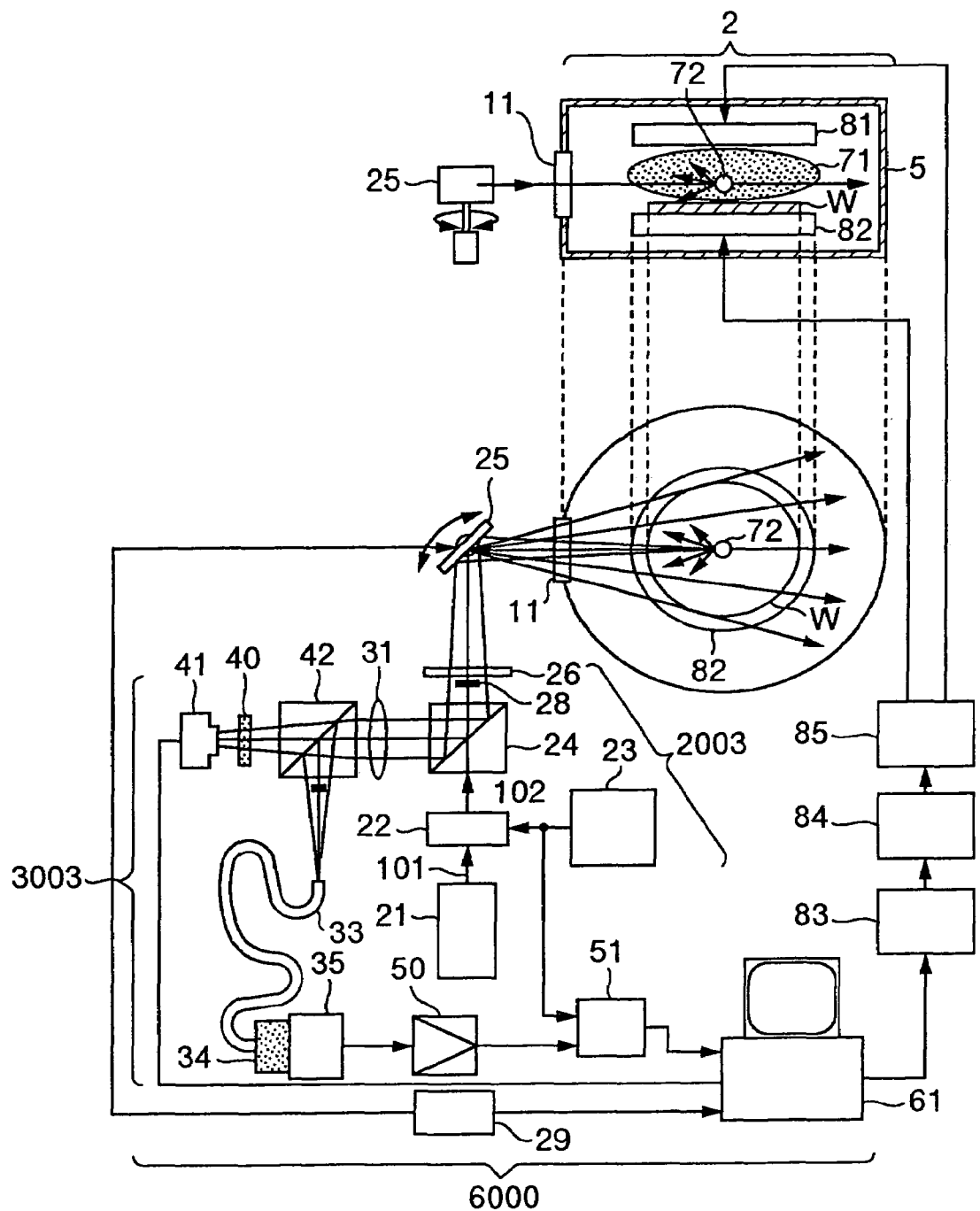
FIG. 13 is an explanatory diagram for illustrating the configuration of an etching processing apparatus having an in-plasma floating particle measuring apparatus relating to a fourth embodiment of the present invention.

FIG. 13 is a diagram for illustrating the configuration of an etching processing apparatus 2 having an in-plasma floating particle measuring apparatus relating to the present 4th embodiment.

The in-plasma floating particle measuring apparatus in the present embodiment basically includes a laser irradiating optical system 2003, a scattered-light detecting optical system 3003, and a signal processing system 6000.

The present embodiment differs from the above-described 3rd embodiment in the following point: In the 3rd embodiment, the reflected-lights from the observing window are light-shielded by using the space filter, whereas, in the present embodiment, the reflected-lights are light-shielded by using a linearly-polarized plate. Since the present embodiment exhibits the effects that are completely identical to those of the 3rd embodiment, the explanation thereof will be given regarding only the point differing from the 3rd embodiment.

As is the case with the 3rd embodiment, an intensity-modulated P-polarized beam passes through a polarization beam splitter 24, and after passing through a linearly-polarized plate 28 installed so that it permits a P-polarized light to pass through, passes through a ¼th-wavelength plate 26, thereby becoming a circularly-polarized beam. After that, the circularly-polarized beam is reflected by a galvanometer mirror 25, then being introduced into a processing chamber 5 through an observing window 11.

Figure 14:
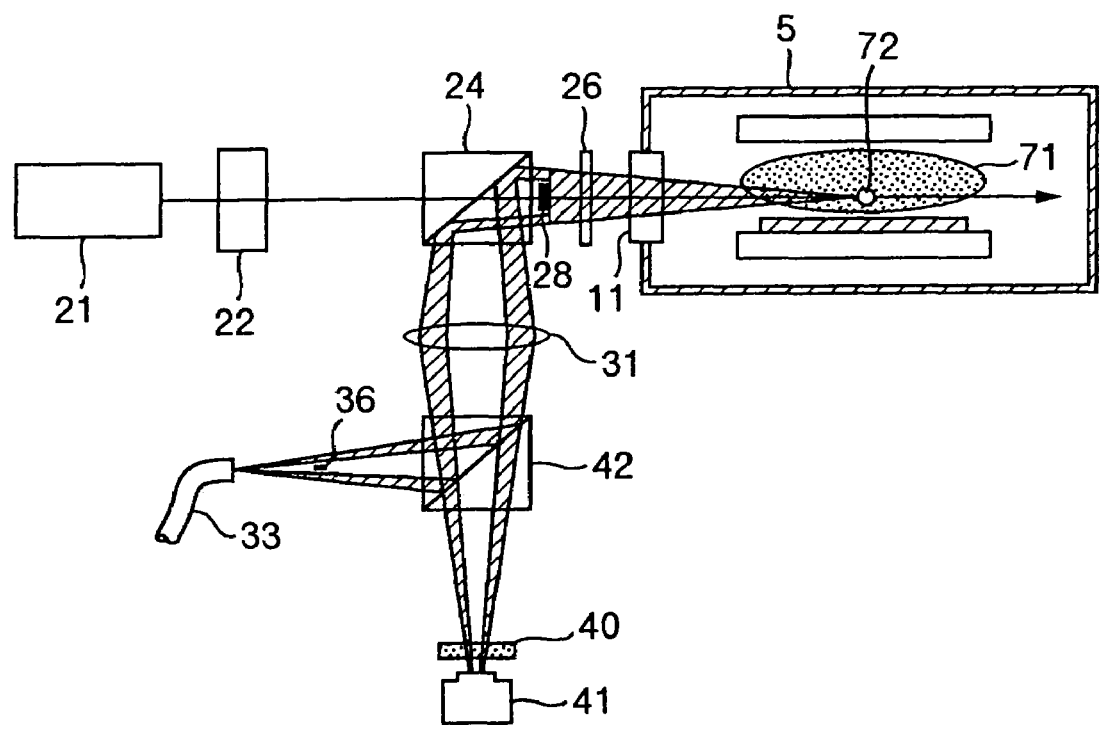
FIG. 14 is an explanatory diagram for illustrating an optical system for detecting the particle scattered-lights in the fourth embodiment of the present invention.

FIG. 14 is a diagram for illustrating a simplified optical path of the observing window reflected-lights and a simplified manner where the scattered-lights are received.

As illustrated in FIGS. 13, 14, the backward scattered-lights generated by floating particles 72 in plasma 71 pass through the observing window 11 and are reflected by the galvanometer mirror 25, then heading for the ¼th-wavelength plate 26. The scattered-lights having passed through the ¼th-wavelength plate 26 are rotated by 90° in the polarization direction and become S-polarized lights. As a result, excluding so small a region where the resultant S-polarized scattered-lights are light-shielded by the linearly-polarized plate 28, the S-polarized scattered-lights are reflected by the polarization beam splitter 24, thereby being detected by the scattered-light detecting optical system.

Meanwhile, the directly reflected-lights from the surface and the rear surface of the observing window 11 also pass through the ¼th-wavelength plate 26, thereby becoming S-polarized lights. As a result, the resultant S-polarized reflected-lights are light-shielded by the linearly-polarized plate 28. Consequently, in the present embodiment as well, as is the case with the above-described 3rd embodiment, the observing window reflected-lights will not be detected.

Also, in the present embodiment as well, as is the case with the above-described 2nd and 3rd embodiments, there are provided with a terminal for outputting the result obtained by the signal processing system to the plasma processing apparatus and so on, and an input terminal for obtaining operating information such as cumulative discharge time from the plasma processing apparatus. This condition permits the in-plasma floating particle measuring apparatus to monitor and control the plasma processing apparatus.

In this way, as is the case with the above-described 2nd and 3rd embodiments, even if the observing window having no special structure generates the reflected-lights, the present embodiment permits the particle scattered-lights to be detected without being subjected to the influences of the reflected-lights.

Also, the present embodiment executes the circularly-polarized irradiation/circularly-polarized detection, thereby allowing the particle scattered-lights to be detected more efficiently as compared with the 1st embodiment.

Next, using FIGS. 15 to 23, the explanation will be given below concerning, as the 5th embodiment, a detecting method and the configuration of an apparatus that take into consideration the influences of the irradiating laser light's reflected-lights from the processing chamber inside-wall surface.

Figure 15:
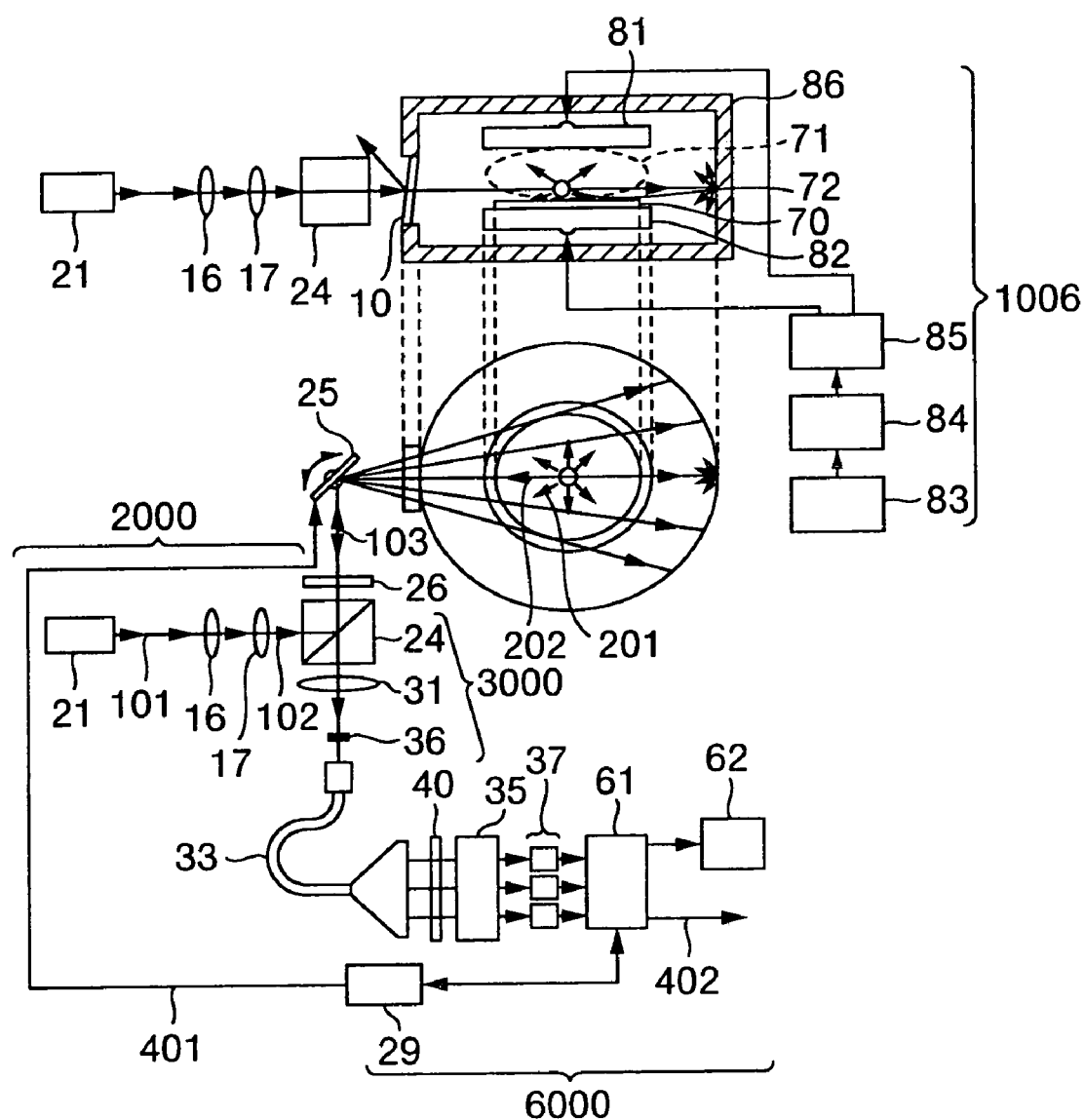
FIG. 15 is a diagram for illustrating an etching apparatus and an in-plasma floating particle measuring apparatus in a fifth embodiment of the present invention.

FIG. 15 is a diagram for illustrating the configuration of an etching apparatus 1006 and an in-plasma floating particle measuring apparatus in the 5th embodiment. The in-plasma floating particle measuring apparatus includes a laser irradiating optical system 2000, a scattered-light detecting optical system 3000, and a signal processing/controlling system 6000.

As illustrated in FIG. 15, in the etching apparatus 1006, the etching is performed as follows: An output voltage from a power amplifier 84 is modulated using a high-frequency signal from a signal generator 83. Next, the resultant high-frequency voltage is distributed by a distributor 85, then being applied between an upper electrode 81 and a lower electrode 82 which are located in parallel to each other inside a plasma processing chamber 86. Moreover, the electrical discharge between both of the electrodes generates plasma 71 from an etching gas. Finally, a to-be-processed target, i.e., a semiconductor wafer 70, is etched by radicals of the plasma.

As the high-frequency signal, there is employed a frequency of an order of, e.g., 400 kHz. When executing the etching processing, the proceeding situation of the etching is monitored so as to detect its endpoint as precisely as possible, thereby performing the etching processing exactly over a predetermined pattern configuration and at a predetermined depth. When the endpoint is detected, the output from a power amplifier 83 is stopped, and then the semiconductor wafer 70 is ejected from the plasma processing chamber 86.

Figure 18:
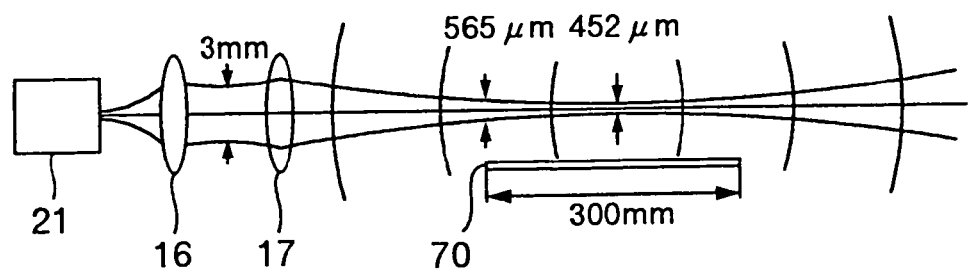
FIG. 18 is a diagram for illustrating the beam spot size directly over a wafer of a light-converged beam by a spherical lens.

In the laser irradiating optical system 2000, at first, a S-polarized beam 101 emitted from a laser 21 (e.g., the 2nd harmonic YAG laser; the wavelength: 532 nm) is expanded by a collimating lens 16, then being light-converged by a focusing lens 17 onto the center of the semiconductor wafer 70. For example, as illustrated in FIG. 18, assuming that the diameter of the incident light into the focusing lens 17 is equal to 3 mm and the focal length of the focusing lens 17 is equal to 2000 mm, the use of a well-known formula in geometrical optics makes it possible to form a light-converged beam the beam spot diameter of which is, on the wafer of ϕ300 mm, 452 μm at a wafer's center and 565 μm at wafer's front and back and the focal depth of which is 602 mm. This light-converged beam allows the particles to be irradiated therewith a substantially uniform optical energy density on the wafer of ϕ300 mm.

The light-converged S-polarized beam 102, after being reflected by a polarization beam splitter 24, is caused to pass through a ¼th-wavelength plate 26, thereby becoming a circularly-polarized beam 103. After that, the circularly-polarized beam 103 is reflected by a high-speed driving galvanometer mirror 25 so as to be introduced into the plasma processing chamber 87 through an observing window 10, thereby scanning the entire plane directly over the semiconductor wafer 70. Scanning the above-described long focal depth beam allows the entire plane directly over the semiconductor wafer 70 to be irradiated with the substantially uniform optical energy density. The circularly-polarized beam 103 is scattered by floating particles 72 in the plasma 71.

Out of the particle scattered-lights 201, the backward scattered-lights 202 scattered in the backward direction along the same optical-axis as that of the incident beam are reflected by the galvanometer mirror 25. The circularly-polarized components, i.e., regular reflection components of the backward scattered-lights, passes through the ¼th-wavelength plate 26 again, thereby being converted into P-polarized components. After that, the P-polarized components pass through the polarization beam splitter 24, then being light-converged by an image-forming lens 31 onto a light-incoming end plane of an optical fiber 33.

Figure 16:
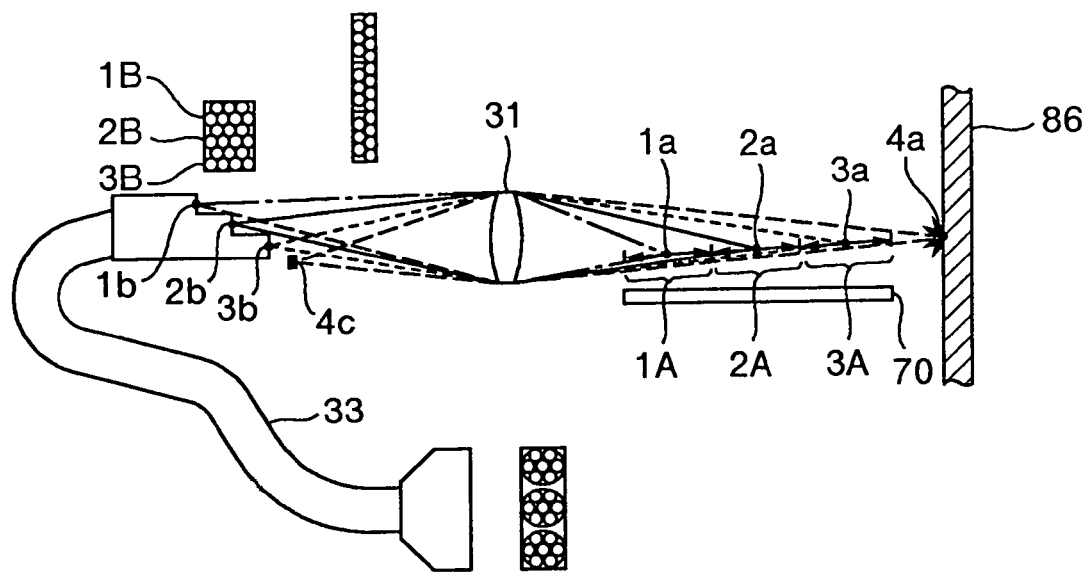
FIG. 16 is a diagram for illustrating the light-reception of the scattered-lights using an axis-shifting detecting optical system and a multi-stage bundle fiber in the fifth embodiment of the present invention.

Here, as illustrated in FIG. 16, the image-forming lens 31 is shifted from a primary light-ray of the propagation optical-axis of the backward scattered-lights. As the result of this operation, the particle scattered-lights from a wafer's front 1a, a wafer's center 2a, and a wafer's back 3a are image-formed at different positions 1b, 2b, and 3b, respectively, instead of being image-formed on one and the same optical-axis. At this time, the light-receiving end plane of the bundle fiber 33 is formed into a multi-step configuration corresponding to the image-formed points 1b, 2b, and 3b. This makes it possible to distinguish and detect the particle scattered-lights from the different points 1a, 2a, and 3a existing in the optical-axis direction of the irradiating light and directly over the semiconductor wafer 70.

Here, the area of the light-receiving plane b1 of the multi-step bundle fiber 33 is made large enough to be able to detect even a defocused particle scattered-light from a region 1A before and behind the point 1a on the wafer. Similarly, the areas of the light-receiving planes b2 and b3 of the multi-step bundle fiber 33 are each made large enough to be able to detect even a defocused particle scattered-light from a region 2A before and behind the point 2a on the wafer and even a defocused particle scattered-light from a region 3A before and behind the point 3a on the wafer. Accordingly, it becomes possible not only to perform the particle detection all over the entire plane directly over the semiconductor wafer 70 in association with the high-speed scanning of the long focal point beam, but also to specify the particle-generated region in the 3 regions in the different optical-axis directions.

Incidentally, in the case where the laser wavelength is equal to 532 nm like the present embodiment, if the particle diameter becomes smaller than about 10 μm, most of the polarized components of the backward scattered-lights become equal to the polarized components of the incident light. Consequently, the employment of the S-polarized irradiation/P-polarized detection (or the P-polarized irradiation/S-polarized detection), which has been widely known as a polarized light separating method, decreases the detected scattered-intensity exceedingly, thus causing a decrease in the detection sensitivity. However, just like the above-described embodiment, the employment of the circularly-polarized irradiation/circularly-polarized detection makes it possible to suppress the decrease in the detection sensitivity associated with the decrease in the particle diameter. Additionally, on account of the shifting of the optical-axis, the directly reflected-lights and the scattered-lights from an irradiation point 4a on the processing chamber inside-wall surface 86 are image-formed at a point 4C outside the light-receiving planes of the multi-step bundle fiber 33, and thus will not be detected.

Figure 17:
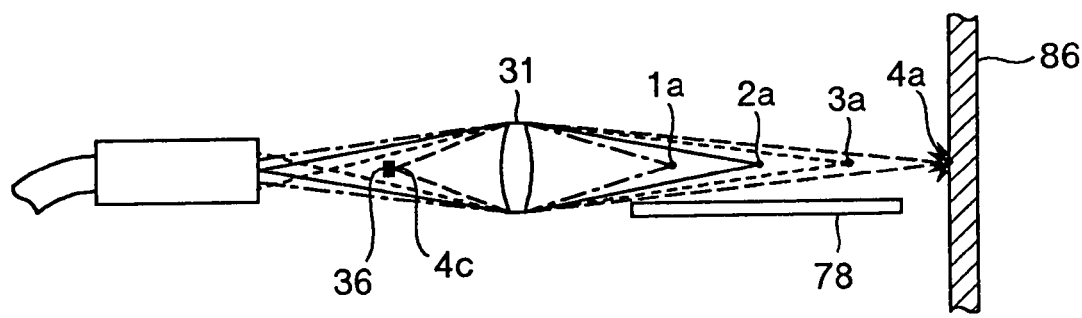
FIG. 17 is a diagram for illustrating the light-reception of the scattered-lights using an image-forming optical system and the bundle fiber.

This is also one of the characteristics of the present invention. Namely, as illustrated in FIG. 17, if the detection optical-axis were not shifted, the image-formed point 4c of the directly reflected-lights and the scattered-lights from the irradiation point 4a on the processing chamber inside-wall 86 would be positioned within the light-flux of the particle scattered-lights from the points 1a and so on that exist directly over the semiconductor wafer 70 to be detected. As a consequence, when using a space filter 36 or the like in order to light-shield the directly reflected-lights and the scattered-lights from the irradiation point 4a on the processing chamber inside-wall 86, a portion of the particle scattered-lights would also be light-shielded simultaneously, thereby resulting in a decrease in the detection sensitivity. On the other hand, in the case where the optical-axis has been shifted just like the present embodiment, there occurs none of the above-described decrease in the detection sensitivity. Concerning the directly reflected-lights from the observing window 10, the observing window 10 is inclined so as to shift the reflection optical-axis from the detection optical-axis, thereby preventing the directly reflected-lights from being launched into the optical fiber. The employment of this configuration is also one of the characteristics of the present invention.

Also, subjecting the observing window to an anti-reflection coating also makes it possible to reduce the intensity of the reflected-lights. The light-emitting end of the fiber 33, which corresponds to the light-receiving end planes of the multi-step bundle fiber 33, are divided in the similar manner. The light-emitting end of the multi-step bundle fiber 33 is connected to an interference filter 40, which extracts the same wavelength component (i.e., 532 nm) as the laser light. Then, a 3-channel 1-dimensional sensor 37 distinguishes the detected lights from the respective light-emitting end planes, thus converting the lights into electrical signals. This makes it possible to specify the particle-generated region in the 3 regions in the different irradiating optical-axis directions.

Instead of the 3-channel 1-dimensional sensor 37, a host diode array of 3-channel parallel output type may also be used. In the signal processing/controlling system 6000, the detected signals from the respective channels of the 3-channel 1-dimensional sensor, after being amplified by a 3-channel amplifier unit 37, are sent to a computer 62. The computer 62 sends a scanning control signal 401 to the galvanometer mirror 25 through a galvano driver 29 and, while thereby scanning the beam 103, the computer displays on a display 62 the particle scattered-intensity at the respective scanning positions.

Figure 19:
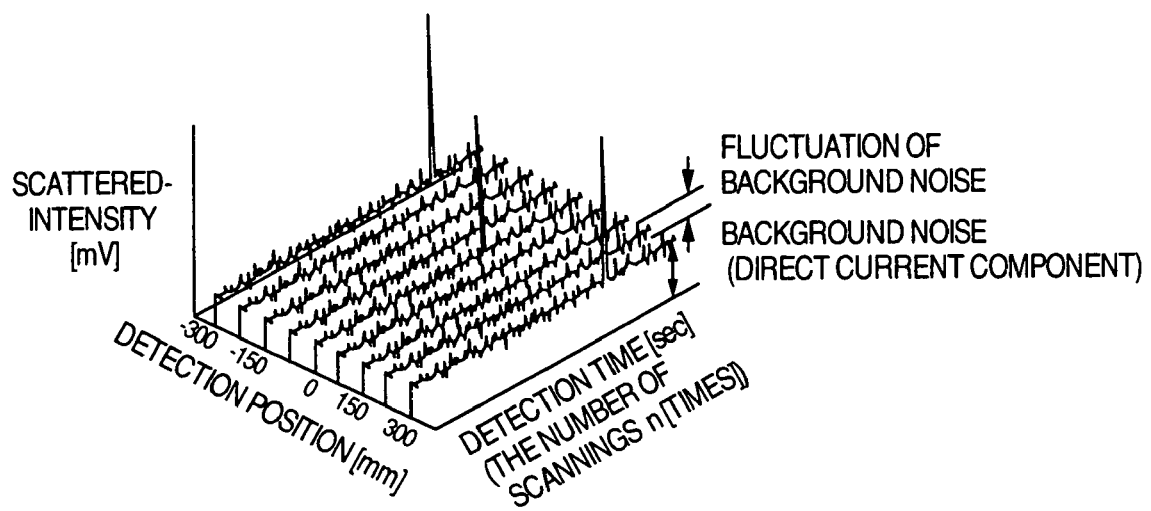
FIG. 19 is a diagram for illustrating time variations in the detected light intensity at 9 points on the wafer in the fifth embodiment of the present invention.
Figure 20:
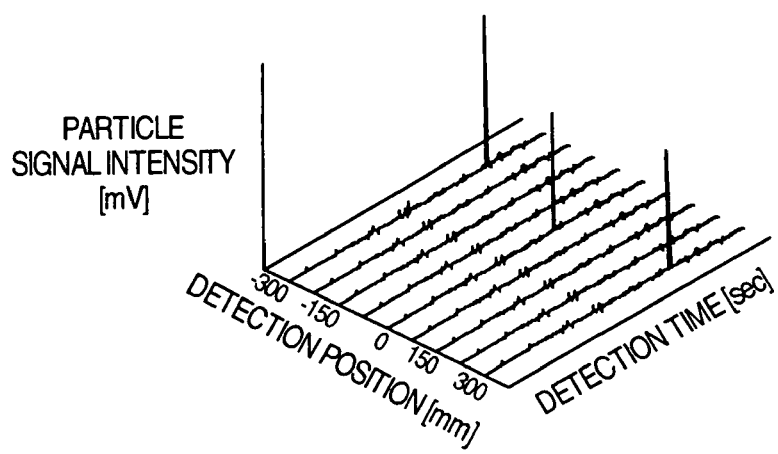
FIG. 20 is a diagram for illustrating time variations in the particle signal intensity at the 9 points on the wafer in the fifth embodiment of the present invention.
Figure 21:
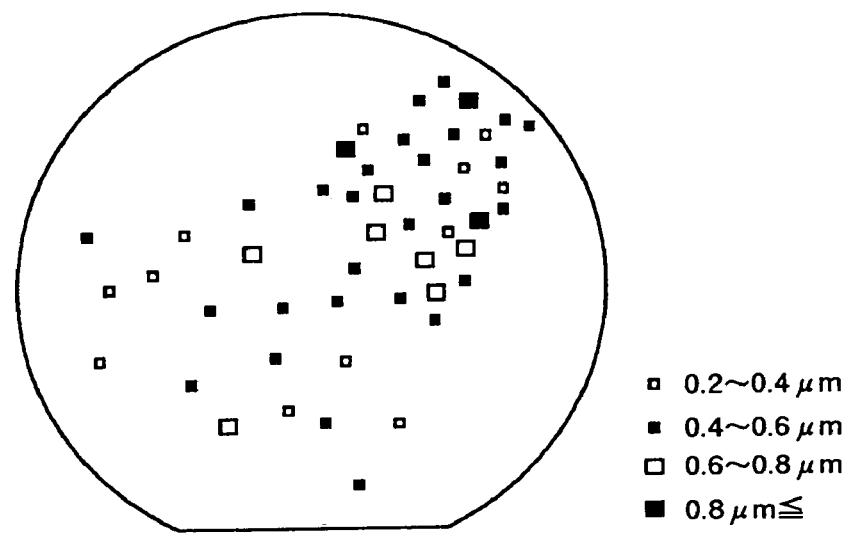
FIG. 21 is a diagram for illustrating the distribution and the size of the generated particles all over the entire surface of the wafer in the fifth embodiment of the present invention.

FIGS. 19 to 21 illustrate displayed examples on the display 62. FIG. 19 illustrates variations for the respective scannings, i.e., the time variations, in the detected signals in the wafer's center region on 9 lines of the irradiating lights on the wafer of ϕ300 mm. When the scattered-lights are generated by the floating particles in the plasma, there appear pulse-like large magnitude of signals as illustrated at 3 positions in FIG. 19. From the intensity of these pulse-like signals, it is possible to judge the size of the particles.

Also, as illustrated in FIG. 20, calculating a difference between the output at the nth time of scanning and the output at the (n−1)th time of scanning at the respective detecting positions makes it possible not only to cancel out the direct current component of the background noise, but also to reduce the fluctuation of the background noise fluctuating similarly all the time, thereby making it easier to judge the particle signals. When the etching is over and the wafer 70 is ejected from the processing chamber, the measurement is terminated. The measured data is recorded on a wafer-to-wafer basis. Outputting the measured data to the outside and utilizing an outside output signal 402 also allows the contamination situation of the plasma processing chamber 87 to be monitored in sequence.

Although, in the present embodiment, the multi-step bundle fiber has been formed into the 3-step configuration, the number of the steps is not limited to 3 and it is possible to select 2 or more of arbitrary number of steps. In the case where the step number is 3 like the present embodiment, on the wafer of, e.g., φ300 mm, the position resolution in the optical-axis direction becomes equal to 100 mm. Meanwhile, for example, setting the bundle fiber's step number to be 10 and the number of the signal processing channels to be 10, the position resolution becomes equal to 30 mm. In this way, increasing the step number makes it possible to enhance the position resolution in the optical-axis direction.

By increasing the step number so as to enhance the position resolution in the optical-axis direction, as illustrated in FIG. 21, it becomes possible to specify the particle-generated position from the position data of the scanning irradiation beam and the particle-generated position data in the irradiating optical-axis directions. Also, it becomes possible to judge the size of the particles in accordance with the signal intensity, thus being capable of mapping the particle-generated distribution on the wafer with the size. From the particle mapping data for each scanning, it becomes possible to guess the behavior of the particles. Based on the data, it becomes possible to obtain information for specifying the particle-generated position inside processing chamber. Moreover, based on the data, it becomes possible to take a reducing countermeasure against the particles inside the processing chamber.

Also, the bundle number and the bundle configuration of the bundle fiber 33 are not limited to the number and the configuration illustrated in FIG. 16. Being able to select arbitrary number and configuration is self-evident.

Figure 22:
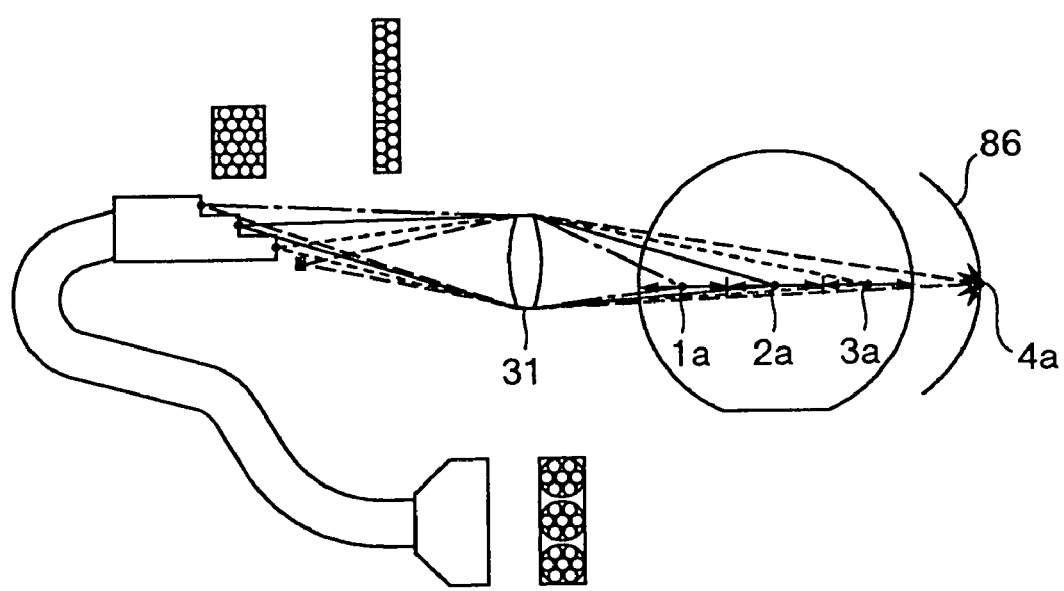
FIG. 22 is a diagram for illustrating a modified example of the light-reception of the scattered-lights using the axis-shifting detecting optical system and the multi-stage bundle fiber in the fifth embodiment of the present invention.

Furthermore, in the present embodiment, although the case has been described where, as illustrated in FIG. 16, the image-forming lens 31 is shifted in an upward direction toward the wafer, it is also self-evident to be able to shift the image-forming lens in a downward direction. Besides, as illustrated in FIG. 22, by shifting the image-forming lens 31 in a direction parallel to the wafer surface, the same effect can also be obtained. This fact indicates that an arbitrary direction can be selected as the direction in which the axis of the image-forming lens 31 is shifted. Also, inclining the image-forming lens makes it possible to obtain the same effect as that of the optical-axis shifting.

Figure 23:
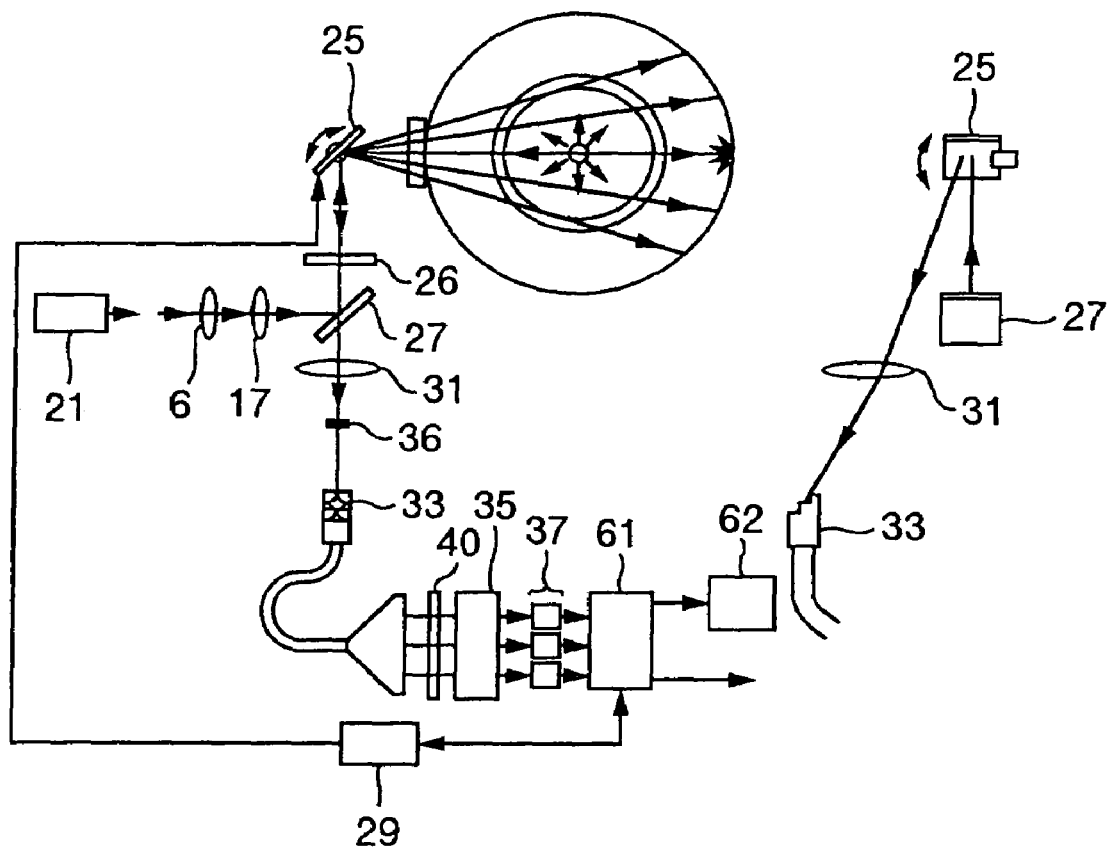
FIG. 23 is a diagram for illustrating the light-reception of the scattered-lights that is performed separating the irradiating optical system from the detecting optical system and using the axis-shifting detecting optical system and the multi-stage bundle fiber in the fifth embodiment of the present invention.

In addition, in the present embodiment, the employment of the detection of the backward scattered-lights permits the irradiation and the scattered-light detection to be executed through the one observing window. This condition allows the irradiating optical system and the detecting optical system to be configured as one unit, thereby making it possible to configure the small-sized optical system. This is also one of the characteristics of the present invention. Conversely, shifting the irradiation optical-axis from the detection optical-axis allows the irradiating optical system and the detecting optical system to be configured in a state of being separated as is illustrated in FIG. 23.

According to the present embodiment, by using the long focal point beam scanning and optical-axis shifting image-forming optical system and the multi-step bundle fiber, there are obtained not only an effect of making it possible to implement the substantially uniform energy irradiation/uniform sensitivity detection all over the entire surface of the wafer, but also an effect of making it possible to specify the particle-generated position all over the entire surface of the wafer.

This effect allows the real-time monitoring of the contamination situation inside the processing chamber of the etching apparatus. This further brings about an effect of being capable of reducing the occurrence of a defective wafer due to the adhering matters, and an effect of being capable of precisely grasping and recognizing a timing for the apparatus cleaning.

Also, it becomes possible to reduce the frequency of a preceding checking operation using a dummy wafer, thereby bringing about an effect of a cost reduction and an enhancement in the productivity.

Even further, since it is possible to specify the particle-generated position, it is possible to specify the particle-generating source by guessing the behavior of the particles. This brings about an effect of being capable of obtaining information that is effective in the reducing countermeasure against the particles.

Figure 24:
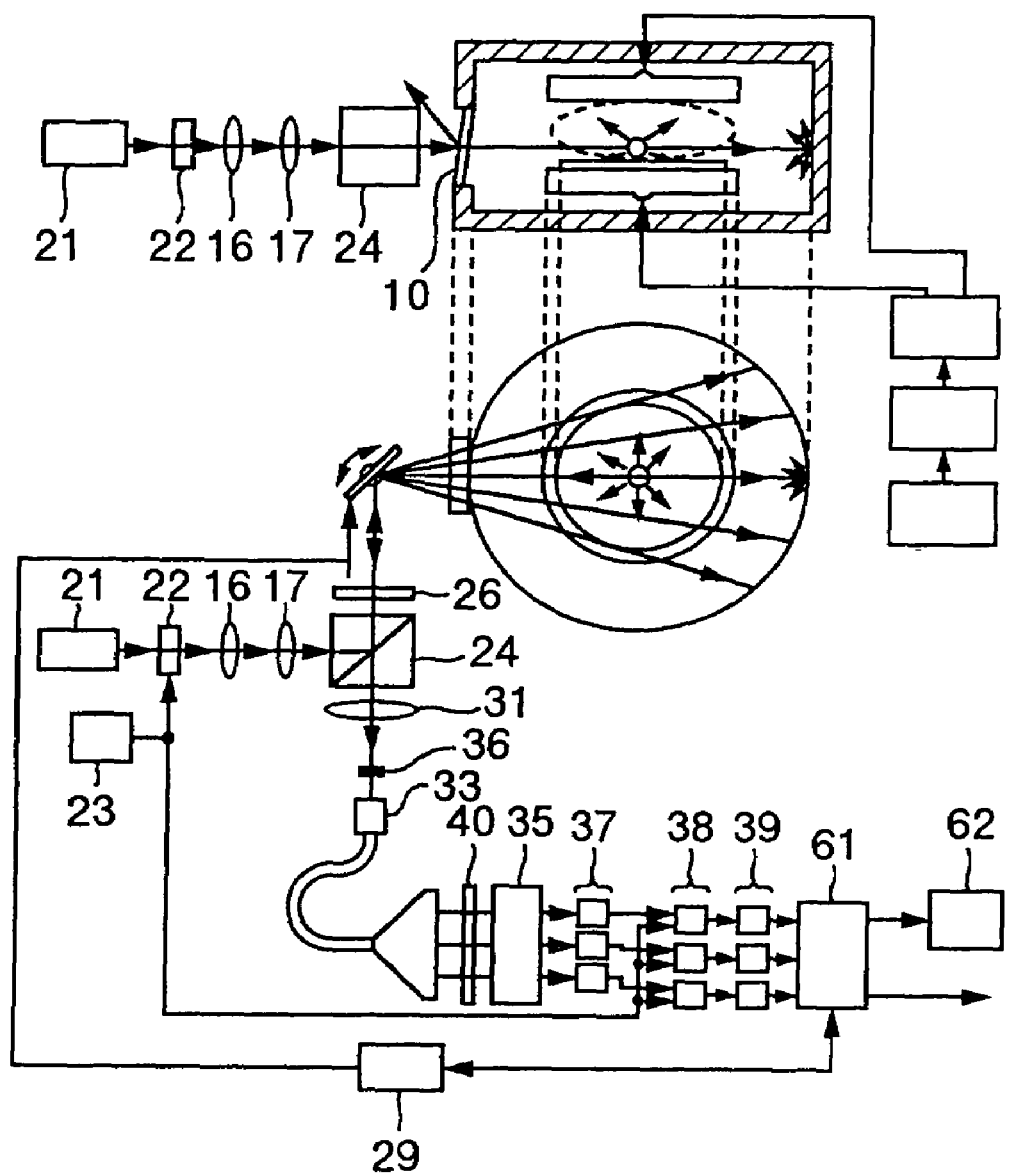
FIG. 24 is a diagram for illustrating an etching apparatus and an in-plasma floating particle measuring apparatus in a sixth embodiment of the present invention.

Next, based on FIG. 24, the explanation will be given below regarding the 6th embodiment of the present invention. In the present embodiment, in the signal processing/controlling system, gain adjusters are provided to subsequent stages of the respective outputs from the 3-channel synchronous detection unit. Since the configuration and the function of the optical system are the same as those in the 5th embodiment, the explanation thereof will be omitted.

The present embodiment makes it possible to obtain the same effect as that of the above-described 5th embodiment. At the same time, the present embodiment allows the exceedingly feeble particle scattered-lights to be detected in a state of being separated from the plasma emitted-light in the two regions of the wavelength and the frequency, which is the same function as having been explained in the above-described 1st embodiment. Accordingly, as compared with the conventional methods of performing the wavelength-separation alone, the present embodiment is capable of tremendously enhancing the detection sensitivity for the in-plasma floating particles, thereby making it possible to detect a particle of an order of φ0.2 μm the detection of which has been impossible by the conventional methods.

Furthermore, the present embodiment makes it possible to correct a decrease in the detection intensity, which is caused by a decrease in the energy density associated with an increase in the beam spot diameter of an irradiating light at the point 1a at the wafer's front or the point 2a at the wafer's back that exists directly over the wafer 70. This brings about an effect of being capable of executing the particle detection with a uniform sensitivity all over the entire surface of the wafer.

Next, based on FIG. 25, the explanation will be given below regarding the 6th embodiment of the present invention.

The present 6th embodiment results from introducing, into photolithography processing steps on the semiconductor producing line, the previously described etching processing apparatus (plasma etching processing apparatus) equipped with the in-plasma floating particle measuring apparatus. FIG. 25 is a diagram for illustrating, schematically and along the processing flow, the photolithography processing steps on the semiconductor producing line.

Figure 25:
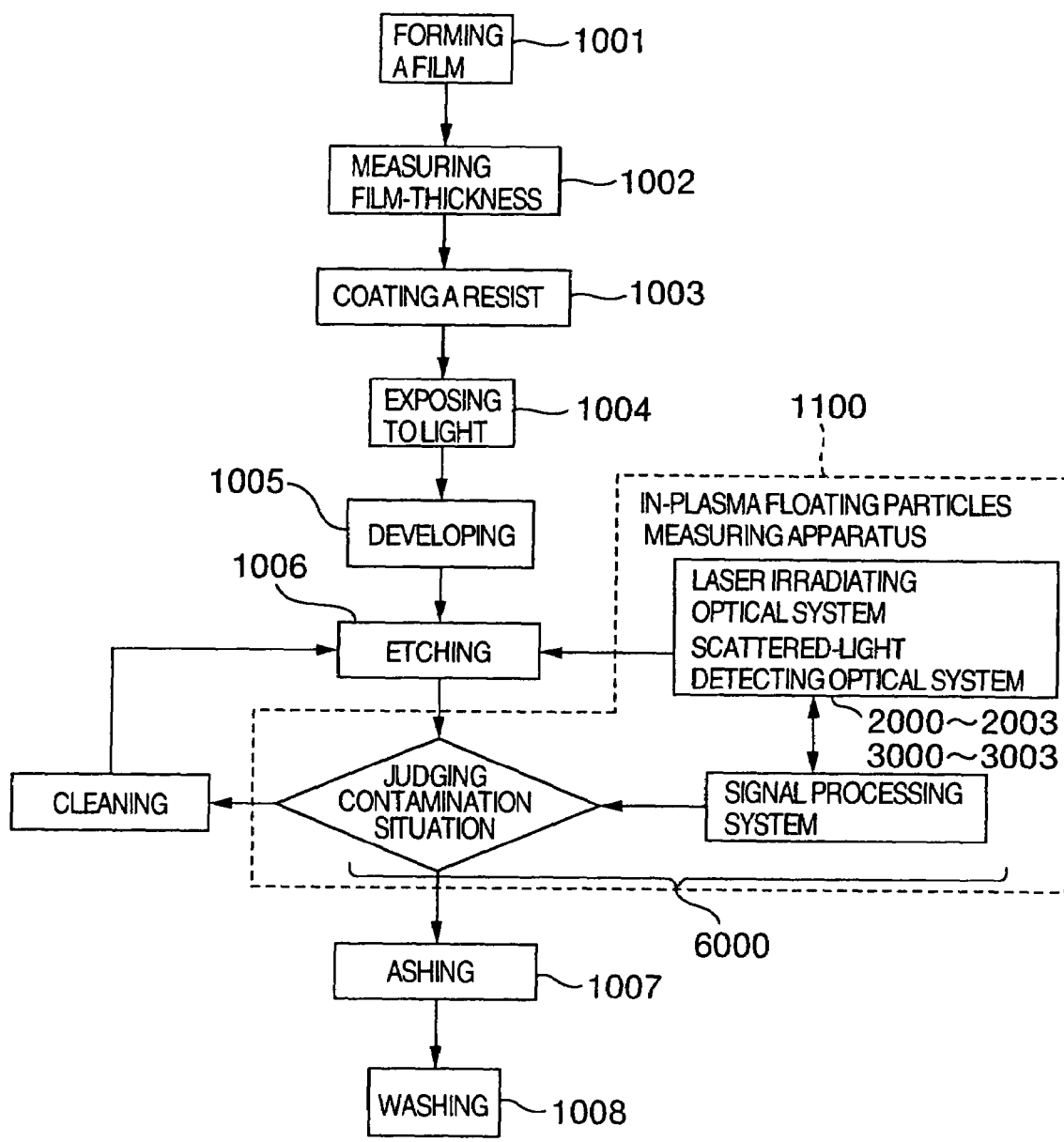
FIG. 25 is an explanatory diagram wherein photolithography processing steps on a semiconductor producing line into which an etching processing apparatus with an in-plasma floating particle measuring apparatus relating to a seventh embodiment of the present invention has been introduced are schematically illustrated along the processing flow.
Figure 26:
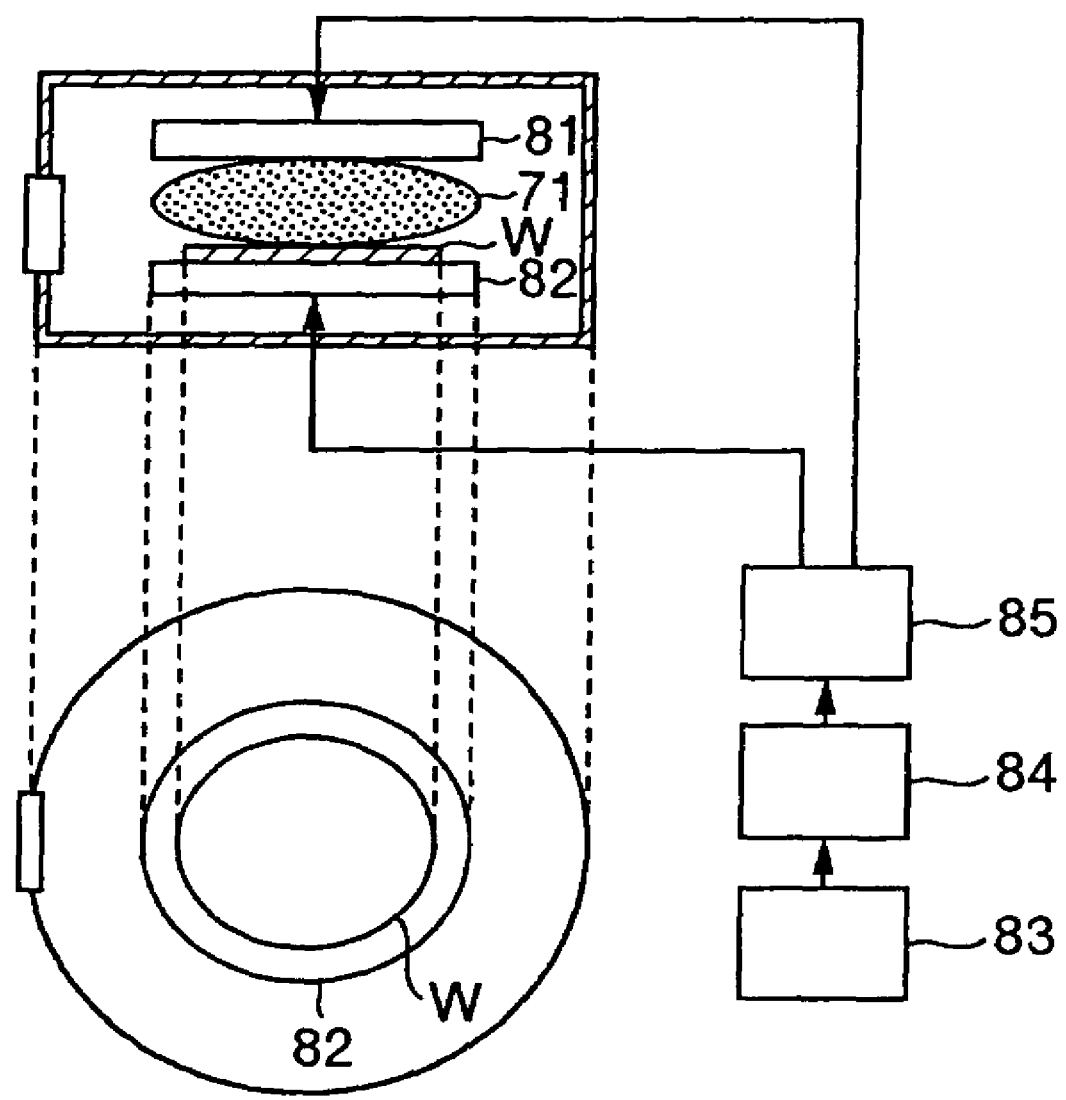
FIG. 26 is an explanatory diagram for illustrating a parallel-plate type plasma etching apparatus.

At first, as illustrated in FIG. 25, a film depositing apparatus 1001 forms, on the wafer, a to-be-processed film such as a silicon oxide film. Next, after a film-thickness measuring apparatus 1002 measures the film-thickness at a plurality of points on the wafer, a resist coating apparatus 1003 coats a resist film. Moreover, an exposure apparatus 1004 transfers a predetermined circuit pattern on a reticle or a mask. A developing apparatus 1005 removes, from the exposed semiconductor wafer, the resist portion corresponding to the transferred pattern.

In addition, with the resultant resist pattern employed as a mask, the etching processing apparatus (plasma etching processing apparatus) 1006 etches the to-be-processed film corresponding to the removed resist portion. The in-plasma floating particle measuring apparatus 1100 detects the particles inside the etching processing apparatus 1006. Based on the signal therefrom, a judging unit in the signal processing system 6000 of the in-plasma floating particle measuring apparatus 1100 judges the contamination situation inside the processing chamber.

If the number of the particles exceeds a predetermined value, the information is informed of the operator of the etching processing apparatus, and cleaning the inside of the processing chamber is performed. If the number of the particles does not exceed the predetermined value, after the etching is over and an ashing apparatus 1007 removes the resist film, the semiconductor wafer is sent to a washing apparatus 1008.

In an etching processing apparatus that is not equipped with the particle monitoring apparatus (i.e., the in-plasma floating particle measuring apparatus 1100), the cleaning of the processing chamber can not necessarily be executed with an appropriate timing. As a result, in some cases, the cleaning is performed at a time where the cleaning need not be performed, thereby reducing the throughput. Conversely, in other cases, the processing is proceeded despite the fact that the time where the cleaning should be performed has passed away, thereby generating a large number of defective products and decreasing the yield.

Also, there exists the method of executing the preceding operation using the dummy wafer for checking the in-processing chamber particles and of determining the cleaning timing from the result. In this case, the extra operation is inserted into the photolithography processing steps, which has decreased the throughput in the photolithography processing steps and has necessitates a cost for the dummy wafer. However, with the wafer diameter becoming larger, an increase in the cost for the dummy wafer is essentially inevitable. Consequently, it has also become a serious problem to reduce the preceding operation using the dummy wafer for checking the in-processing chamber particles.

In contrast to this, according to present embodiment, it is possible to execute the processing of the to-be-processed target while monitoring the contamination situation inside the processing chamber in real time. This condition accomplishes the optimization at the timing for the cleaning and thus eliminates the necessity for the preceding operation using the dummy wafer, which enhances the throughput and allows the cost reduction in the dummy wafer. Also, the products manufactured in the processing steps in the present embodiment turn out to become the high-quality products containing only the particles the number of which is smaller than the predetermined value.

Incidentally, although, in the previously described embodiments, the examples applied to the etching processing apparatus have been explained, the application range of the present invention is not limited thereto. For example, the present invention is applied to the ashing apparatus or the film forming apparatuses, thereby allowing the real-time monitoring of the particles inside the ashing apparatus or the thin-film forming apparatuses. This eventually makes it possible to reduce the defects caused by the ashing processing step or the film forming processing step in the photolithography processing steps, thereby being able to prevent the occurrence of the defective products and to enhance the yield.

As having been explained so far, in the present embodiment, the employment of the detection of the backward scattered-lights permits the irradiating optical system and the detecting optical system to be configured as one unit, thereby making it possible to implement the particle detecting apparatus that is small-sized and is easy to mount and adjust.

Also, the present embodiment never detects the reflected-lights from the observing window's surface and the processing chamber inside-wall scattered-lights, which are likely to become loud noises in the detection of the backward scattered-lights. Moreover, the present embodiment allows the exceedingly feeble particle scattered-lights to be, detected in a state of being separated from the plasma emitted-light noise that becomes a problem in the detection of the in-plasma particles. This enhances the detection sensitivity, thereby making it possible to detect the microscopic particles of the submicron order which are expected to be difficult to detect using the conventional methods.

Moreover, in the present embodiment, the configuration is employed where the irradiating light can be scanned, and further the configuration is employed where the irradiating/detecting optical system can be slid in the up-and-down direction. This condition makes it possible not only to observe the different plasma regions, but also to execute the detection of the particles all over the entire surface of the wafer so as to judge the number, the size, and the distribution of the particles. This permits the operator to confirm the information in real time on the display.

In addition, according to present embodiment, based on the information about the number, the size, and the distribution of the generated particles, it is possible to judge the contamination situation inside the processing chamber in real time. This condition not only accomplishes the optimization at the timing for the cleaning so as to enhance the throughput, but also prevents the occurrence of the excursion so as to enhance the yield. Also, it is possible to proceed the processing while monitoring all the time the number of the particles inside the processing chamber. As a result, the circuit board manufactured in this way turn out to become high-quality and high-reliability products containing only the particles the number of which is smaller than a reference value.

Also, according to present embodiment, there exist no necessities for the contamination situation judgement on the processing chamber with the use of a dummy wafer and the contamination situation judgement based on an extraction inspection. This condition brings about a cost reduction in the dummy wafer and the enhancement in the throughput.

Furthermore, in the present embodiment, the employment of the long focal point beam and the optical-axis shifting multi-step detection makes it possible to detect the number of the particles and the particle-generated position all over the entire surface of the wafer. This, in comparison with the conventional methods, allows the detailed judgement to be performed on the generation situation of the in-plasma floating particles.

Also, it is possible to use the long focal point beam and the optical-axis shifting multi-step detection together with the method of detecting the exceedingly feeble particle scattered-lights in a state of being separated from the plasma emitted-light in the two regions of the wavelength and the frequency. As a result, the present embodiment is capable of tremendously enhancing the detection sensitivity for the in-plasma floating particles in comparison with the conventional methods, and is capable of detecting the number of the particles and the particle-generated position all over the entire surface of the wafer. This, in comparison with the conventional methods, allows the detailed judgement to be stably performed on the generation situation of the in-plasma floating particles.

Still further, the gain adjusting function is added to the respective channels of the outputting unit for the optical-axis shifting multi-step detection. This makes it possible to correct a variation in the detection sensitivity due to a difference in the irradiation energies of the illuminating beams, thereby allowing the floating particles to be detected stably and with a uniform detection sensitivity all over the entire surface of the wafer.

These effects allow the real-time monitoring of the contamination situation inside the etching processing chamber. This further brings about an effect of being capable of reducing the occurrence of a defective wafer due to the adhering matters, and an effect of being capable of precisely grasping and recognizing a timing for the apparatus cleaning.

Also, it becomes possible to reduce the frequency of a preceding checking operation using a dummy wafer, thereby bringing about an effect of a cost reduction and an enhancement in the productivity. Also, there is provided an effect of making it possible to antomate the production line.

INDUSTRIAL APPLICABILITY

As having been explained so far, in the present embodiment, the employment of the detection of the backward scattered-lights permits the irradiating optical system and the detecting optical system to be configured as one unit, thereby making it possible to implement the particle detecting apparatus that is small-sized and is easy to mount and adjust.

Also, the present embodiment never detects the reflected-lights from the observing window's surface and the processing chamber inside-wall scattered-lights, which are likely to become loud noises in the detection of the backward scattered-lights. Moreover, the present embodiment allows the exceedingly feeble particle scattered-lights to be detected in a state of being separated from the plasma emitted-light noise that becomes a problem in the detection of the in-plasma particles. This enhances the detection sensitivity, thereby making it possible to implement the particle detecting apparatus that is capable of detecting the microscopic particles of the submicron order which are expected to be difficult to detect using the conventional methods.

Moreover, in the present embodiment, the configuration is employed where the irradiating light can be scanned, and further the configuration is employed where the irradiating/detecting optical system can be slid in the up-and-down direction. This condition makes it possible not only to observe the different plasma regions, but also to execute the detection of the particles all over the entire surface of the wafer so as to judge the number, the size, and the distribution of the particles. Accordingly, it is possible to implement the particle detecting apparatus that permits the operator to confirm the information in real time on the display.

Furthermore, according to present embodiment, based on the information about the number, the size, and the distribution of the generated particles, it is possible to judge the contamination situation inside the processing chamber in real time. This condition makes it possible to judge the optimum timing for the cleaning, thereby allowing a semiconductor device to be fabricated with a high-throughput and an excellent-yield.

Also, it is possible to proceed the processing while monitoring all the time the number of the particles inside the processing chamber. Consequently, the present invention is applicable to the production of the high-quality and high-reliability circuit board containing only the particles the number of which is smaller than a reference value.

The invention claimed is:

1. A circuit board producing method in executing, inside a processing chamber, a treatment of forming a thin-film on a to-be-processed target or a treatment of processing said thin-film formed on said to-be-processed target, comprising the steps of:
  performing an irradiation with a laser light into said processing chamber through an observing window, said laser light having a desired polarization and a desired wavelength and being intensity-modulated with a desired frequency,
    wavelength-separating and light-receiving a light of a wavelength component of said frequency out of backward scattered-lights that have been scattered by particles inside said processing chamber through said irradiation and that have passed through said observing window,
  detecting said frequency component out of said light-received signal obtained by being light-received,
  obtaining, using said detected signal, information about number and size of said particles existing in a region irradiated with said laser light inside said processing chamber, and
  outputting said obtained information about said number and said size of said particles.

2. The circuit board producing method as claimed in claim 1, further comprising the steps of:
  wavelength-separating, light-receiving, and image-photographing said light of said wavelength component out of said backward scattered-lights that have been scattered by said particles inside said processing chamber and that have passed through said observing window,
  detecting said frequency component out of said light-received signal obtained by being light-received, and
  judging at least one of said number, said size, and distribution of said particles by using said detected signal obtained by being detected and said image obtained by being image-photographed.

3. The circuit board producing method as claimed in claim 1, wherein said desired polarization of said laser light is P-polarized state, an irradiation with said P-polarized laser beam being performed into said processing chamber through said observing window that is inclined in such a manner as to form Brewster angle toward said P-polarized laser beam.

4. The circuit board producing method as claimed in claim 1, wherein a 2-dimensional distribution of said particles is judged by executing a rotation scanning of said irradiating beam in a horizontal direction, said irradiation with said irradiating beam being performed into said processing chamber through said observing window.

5. The circuit board producing method as claimed in claim 1, wherein said desired frequency differs from a frequency of an exciting source and its integer-multiples, said exciting source being used for said thin-film forming treatment or said thin-film processing treatment.

6. A circuit board producing method, comprising the steps of:
- applying a high-frequency voltage to electrodes inside a processing chamber in a state where a to-be-processed target has been transferred into said processing chamber, and generating plasma inside said processing chamber so as to process said to-be-processed target,
- introducing a laser light into said processing chamber through an observing window so as to irradiate, with said laser light, a region directly over said to-be-processed target that is being processed by said plasma, said laser light being intensity-modulated with a desired frequency,
- detecting scattered-lights that have been scattered by particles inside said processing chamber through said irradiation and that have passed through said observing window,
- obtaining, from said detected scattered-lights, information about said particles existing in said region directly over said to-be-processed target, said region having been irradiated with said laser light, and
- outputting said obtained information about said particles.

7. The circuit board producing method as claimed in claim 6, wherein, from said scattered-lights that have passed through said observing window, a light of a wavelength component of said desired frequency is wavelength-separated and detected through a filter.

8. The circuit board producing method as claimed in claim 6, further comprising a step of obtaining, from said detected scattered-lights, information about size and distribution of said particles existing in said region directly over said to-be-processed target.

9. A circuit board producing method, comprising the steps of:
- generating plasma inside a processing chamber so as to process a to-be-processed target set inside said processing chamber,
- introducing, in a middle of processing said to-be-processed target, a laser light into said processing chamber through an observing window so as to irradiate, with said laser light, a region directly over said to-be-processed target that is being processed by said plasma,
- detecting scattered-lights in such a manner as to be separated from an emitted-light emitted from said plasma, said scattered-lights having been scattered by particles inside said processing chamber through said irradiation and having passed through said observing window,
- determining, from said detected scattered-lights, information about size and distribution of at least said particles existing in said region directly over said to-be-processed target, and
- displaying, on a monitor screen, said determined information about said size and said distribution of said particles existing in said region directly over said to-be-processed target.

10. The circuit board producing method as claimed in claim 9, wherein said scattered-lights are detected in such a manner as to be separated from a reflected-light reflected from a wall surface of said processing chamber, said scattered-lights having been scattered through said irradiation by said particles floating inside said processing chamber.

11. The circuit board producing method as claimed in claim 9, wherein, while monitoring a contamination situation inside said processing chamber in accordance with said information about said size and said distribution of said particles, a treatment of forming a thin-film on said to-be-processed target or a treatment of processing said thin-film formed on said to-be-processed target is executed inside said processing chamber.

* * * * *